United States Patent
Frendewey et al.

(10) Patent No.: US 10,301,646 B2
(45) Date of Patent: *May 28, 2019

(54) NUCLEASE-MEDIATED TARGETING WITH LARGE TARGETING VECTORS

(71) Applicant: Regeneron Pharmaceuticals, Inc., Tarrytown, NY (US)

(72) Inventors: David Frendewey, New York, NY (US); Wojtek Auerbach, Ridgewood, NJ (US); David M. Valenzuela, Yorktown Heights, NY (US); George D. Yancopoulos, Yorktown Heights, NY (US); Ka-Man Venus Lai, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/792,112

(22) Filed: Oct. 24, 2017

(65) Prior Publication Data

US 2018/0037910 A1    Feb. 8, 2018

Related U.S. Application Data

(63) Continuation of application No. 13/870,280, filed on Apr. 25, 2013, now Pat. No. 9,834,786.

(60) Provisional application No. 61/638,267, filed on Apr. 25, 2012.

(51) Int. Cl.
*C12N 15/85* (2006.01)
*C07K 14/715* (2006.01)
*C12N 15/90* (2006.01)

(52) U.S. Cl.
CPC .......... *C12N 15/85* (2013.01); *C07K 14/7155* (2013.01); *C12N 15/8509* (2013.01); *C12N 15/907* (2013.01)

(58) Field of Classification Search
CPC .. C12N 15/85; C12N 15/8509; C12N 15/907; C07K 14/7155
See application file for complete search history.

(56) References Cited

U.S. PATENT DOCUMENTS

| | | |
|---|---|---|
| 6,372,956 B1 | 4/2002 | Goldsmith et al. |
| 6,566,579 B1 | 5/2003 | Jaisser et al. |
| 7,294,754 B2 | 11/2007 | Poueymirou et al. |
| 7,771,967 B2 | 8/2010 | Huang et al. |
| 8,502,018 B2 | 8/2013 | Murphy et al. |
| 8,558,055 B2 | 10/2013 | Ostertag et al. |
| 8,697,359 B1 | 4/2014 | Zhang |
| 8,703,485 B2 | 4/2014 | Buelow |
| 8,722,964 B2 | 5/2014 | Ostertag et al. |
| 8,907,157 B2 | 12/2014 | Buelow |
| 8,921,332 B2 | 12/2014 | Choulika et al. |
| 9,228,208 B2 | 1/2016 | Frendewey et al. |
| 9,834,786 B2 | 12/2017 | Frendewey et al. |
| 2002/0106628 A1 | 8/2002 | Economides et al. |
| 2002/0106629 A1 | 8/2002 | Murphy et al. |
| 2002/0183275 A1 | 12/2002 | Murphy et al. |
| 2003/0134318 A1 | 7/2003 | Case et al. |
| 2003/0175968 A1 | 9/2003 | Golic et al. |
| 2003/0232410 A1 | 12/2003 | Liljedahl et al. |
| 2004/0018626 A1 | 1/2004 | Murphy et al. |
| 2004/0197317 A1 | 10/2004 | Rao et al. |
| 2005/0026157 A1 | 2/2005 | Baltimore et al. |
| 2005/0064474 A1 | 3/2005 | Urnov et al. |
| 2005/0144655 A1 | 6/2005 | Economides et al. |
| 2005/0208489 A1 | 9/2005 | Carroll et al. |
| 2006/0063231 A1 | 3/2006 | Li et al. |
| 2006/0085866 A1 | 4/2006 | Poueymirou et al. |
| 2006/0188987 A1 | 8/2006 | Guschin et al. |
| 2008/0028479 A1 | 1/2008 | Poueymirou et al. |
| 2008/0066197 A1 | 3/2008 | Ying et al. |
| 2008/0078000 A1 | 3/2008 | Poueymirou et al. |
| 2008/0078001 A1 | 3/2008 | Poueymirou et al. |
| 2008/0113437 A1 | 5/2008 | Joly et al. |
| 2008/0299580 A1 | 12/2008 | DeKelver et al. |
| 2009/0055943 A1 | 2/2009 | Economides et al. |
| 2010/0047805 A1 | 2/2010 | Wang |
| 2010/0076057 A1 | 3/2010 | Sontheimer et al. |
| 2010/0218264 A1 | 8/2010 | Cui et al. |
| 2011/0104799 A1 | 5/2011 | Economides et al. |
| 2011/0145940 A1 | 6/2011 | Voytas et al. |
| 2011/0207221 A1 | 8/2011 | Cost et al. |
| 2011/0239315 A1 | 9/2011 | Bonas et al. |
| 2011/0263028 A1 | 10/2011 | Cabaniols et al. |
| 2011/0269234 A1 | 11/2011 | Doyon |
| 2011/0307968 A1 | 12/2011 | Auerbach et al. |
| 2012/0272349 A1 | 10/2012 | Ochiya et al. |
| 2012/0315670 A1 | 12/2012 | Jacobson et al. |
| 2013/0309670 A1 | 11/2013 | Frendewey et al. |

(Continued)

FOREIGN PATENT DOCUMENTS

| | | |
|---|---|---|
| EP | 2336329 A1 | 6/2011 |
| EP | 2152880 B1 | 8/2011 |

(Continued)

OTHER PUBLICATIONS

"Stem Cells: Scientific Progress and Future Research Directions," National Institute of Health, Department of Health and Human Services, (2001).

(Continued)

*Primary Examiner* — Titilayo Moloye
(74) *Attorney, Agent, or Firm* — Yongjin Choi; Alston & Bird LLP

(57) ABSTRACT

Compositions and methods are provided for making one or more targeted genetic modifications at a target genomic locus by employing homologous recombination facilitated by single or double-strand break at or near the target genomic locus. Compositions and methods for promoting efficiency of homologous recombination between an LTVEC and a target genomic locus in prokaryotic or eukaryotic cells using engineered nucleases are also provided.

28 Claims, 1 Drawing Sheet
Specification includes a Sequence Listing.

(56) References Cited

U.S. PATENT DOCUMENTS

| | | |
|---|---|---|
| 2014/0068797 A1 | 3/2014 | Doudna et al. |
| 2014/0179770 A1 | 6/2014 | Zhang et al. |
| 2014/0186843 A1 | 7/2014 | Zhang et al. |
| 2014/0186958 A1 | 7/2014 | Zhang et al. |
| 2014/0235933 A1 | 8/2014 | Lee et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0273037 A1 | 9/2014 | Wu |
| 2014/0273226 A1 | 9/2014 | Wu |
| 2014/0273231 A1 | 9/2014 | Zhang et al. |
| 2014/0273232 A1 | 9/2014 | Zhang et al. |
| 2014/0273233 A1 | 9/2014 | Chen et al. |
| 2014/0273234 A1 | 9/2014 | Zhang et al. |
| 2014/0301990 A1 | 10/2014 | Gregory et al. |
| 2014/0309487 A1 | 10/2014 | Lee et al. |
| 2014/0310828 A1 | 10/2014 | Lee et al. |
| 2014/0315985 A1 | 10/2014 | May et al. |
| 2014/0342456 A1 | 11/2014 | Mali et al. |
| 2014/0342458 A1 | 11/2014 | Mali et al. |
| 2014/0349400 A1 | 11/2014 | Jakimo et al. |
| 2015/0031133 A1 | 1/2015 | Church et al. |
| 2015/0071889 A1 | 3/2015 | Musunuru et al. |
| 2015/0159174 A1 | 6/2015 | Frendewey et al. |
| 2015/0159175 A1 | 6/2015 | Frendewey et al. |
| 2015/0176013 A1 | 6/2015 | Musunuru et al. |
| 2015/0283265 A1 | 10/2015 | Peyman |
| 2015/0291965 A1 | 10/2015 | Zhang et al. |
| 2015/0291966 A1 | 10/2015 | Zhang et al. |
| 2015/0376650 A1 | 12/2015 | Auerbach et al. |
| 2015/0376651 A1 | 12/2015 | Frendewey et al. |
| 2016/0024529 A1 | 1/2016 | Carstens |
| 2016/0040155 A1 | 2/2016 | Maizels et al. |
| 2016/0046960 A1 | 2/2016 | Frendewey et al. |
| 2016/0060637 A1 | 3/2016 | Hommelsheim et al. |
| 2016/0060657 A1 | 3/2016 | Frendewey et al. |
| 2016/0138046 A1 | 5/2016 | Wu |
| 2016/0151491 A1 | 6/2016 | Rabinovich et al. |
| 2016/0177339 A1 | 6/2016 | Voronina et al. |
| 2016/0257967 A1 | 9/2016 | Russell et al. |

FOREIGN PATENT DOCUMENTS

| | | |
|---|---|---|
| EP | 1360287 B1 | 9/2012 |
| EP | 2602323 A1 | 6/2013 |
| EP | 3064585 A1 | 9/2016 |
| WO | WO 1998/041645 A1 | 9/1998 |
| WO | WO 2002/036789 A2 | 5/2002 |
| WO | WO 2002/066630 A1 | 8/2002 |
| WO | WO 2003/087341 A2 | 10/2003 |
| WO | WO 2005/014791 A2 | 2/2005 |
| WO | WO 2006/044962 A1 | 4/2006 |
| WO | WO 2007/117410 A2 | 10/2007 |
| WO | WO 2008/151081 A1 | 12/2008 |
| WO | WO 2011/051390 A1 | 5/2011 |
| WO | WO 2011/078665 A1 | 6/2011 |
| WO | WO 2011/146121 A1 | 11/2011 |
| WO | WO 2011/154927 A2 | 12/2011 |
| WO | WO 2012/012667 A2 | 1/2012 |
| WO | WO 2012/018726 A1 | 9/2012 |
| WO | WO 2012/129198 A1 | 9/2012 |
| WO | WO 2012/168307 A2 | 12/2012 |
| WO | WO 2013/063361 A1 | 5/2013 |
| WO | WO 2013/141680 A1 | 9/2013 |
| WO | WO 2013/142578 A1 | 9/2013 |
| WO | WO 2013/163394 A1 | 10/2013 |
| WO | WO 2013/169802 A1 | 11/2013 |
| WO | WO 2013/176772 A1 | 11/2013 |
| WO | WO 2013/188522 A2 | 12/2013 |
| WO | WO 2014/018423 A2 | 1/2014 |
| WO | WO 2014/065596 A1 | 5/2014 |
| WO | WO 2014/089290 A1 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/127287 A1 | 8/2014 |
| WO | WO 2014/130706 A1 | 8/2014 |
| WO | WO 2014/130955 A1 | 8/2014 |
| WO | WO 2014/131833 A1 | 9/2014 |
| WO | WO 2014/143381 A1 | 9/2014 |
| WO | WO 2014/150624 A1 | 9/2014 |
| WO | WO 2014/165825 A2 | 10/2014 |
| WO | WO 2014/172458 A1 | 10/2014 |
| WO | WO 2014/172470 A2 | 10/2014 |
| WO | WO 2014/172489 A2 | 10/2014 |
| WO | WO 2014/173955 A1 | 10/2014 |
| WO | WO 2015/088643 A1 | 6/2015 |
| WO | WO 2015/188109 A1 | 12/2015 |
| WO | WO 2015/200805 A2 | 12/2015 |
| WO | WO 2016/011210 A2 | 1/2016 |

OTHER PUBLICATIONS

Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.

Barrangou, "RNA-mediated programmable DNA cleavage," Nature Biotechnology, 2012, vol. 30(9), pp. 836-838.

Benders et al., "Cloning whole bacterial genomes in yeast," Nucleic Acids Res., vol. 38(8), pp. 2558-2569, Mar. 7, 2010.

Berdien, et al., "TALEN-mediated editing of endogenous T-cell receptors facilitates efficient reprogramming of T lymphocytes by lentiviral gene transfer," Gene Therapy, 21, 539-548 (2014).

Beumer et al., "Donor DNA Utilization During Gene Targeting with Zinc-Finger Nucleases," Genes Genomes Genetics, vol. 3, pp. 657-664, Apr. 2013.

Brouns, S.J.J., "A Swiss Army Knife of Immunity," Science (2012), vol. 337, pp. 808-809.

Carlson, et al., "Targeting DNA with Fingers and TALENs," Molecular Therapy-Nucleic Acids, 2012, 1:e3.

Carroll, "Staying on target with CRISPR-Cas," Nature Biotechnology, 2013, vol. 31(9), pp. 807-809.

Carroll, "Zinc-Finger Nucleases as Gene Therapy Agents", Gene Ther., Nov. 15, 2008:(22):1463-1468.

Cathomen, et al., "Zinc-finger nucleases: the next generation emerges," Molecular Therapy, 208, vol. 16(7), pp. 1200-1207 (Jul. 2008).

Chang et al., "Genome editing with RNA-guided Cas9 nuclease in Zebrafish embryos," Cell Research, vol. 23, pp. 465-472, 2013. (published Mar. 2013).

Chen et al., "High-frequency genome editing using ssDNA oligonucleotides with zinc-finger nucleases," Nature Methods, vol. 8(9), pp. 753-755, 2011. (Jul. 17, 2011).

Cho, et al., "Targeting genome engineering in human cells with the Cas9 RNA-guided endonuclease," Nature Biotechnology, 2013, vol. 31(3):233-239.

Choulika et al., "Induction of Homologous Recombination in Mammalian Chromosomes by Using the I-SceI System of *Saccharomyces cerevisiae*," Mol. Cell. Biol., vol. 15(4), pp. 1968-1973, 1995.

Christian M., et al., "Targeting DNA Double-Strand Breaks with TAL Effector Nucleases," Genetics (2010), vol. 186, pp. 757-761.

Christian, et al., "Targeting DNA double-strand breaks with TAL effector nucleases," Genetics, 2010, vol. 186, pp. 757-761.

Cobb and Zhao, "Direct cloning of large genomic sequences," Nature Biotechnology, 2012, vol. 30(5), pp. 405-406.

Cong et al., "Multiplex Genome Engineering Using CRISPR/Cas Systems," Science, vol. 339(6121), pp. 819-823 plus Supplemental Materials, Jan. 3, 2013.

(56) References Cited

OTHER PUBLICATIONS

Cong, et al., "Multiplex genome engineering using CRISPR/Cas systems," Science, 2013, vol. 339(6121), pp. 819-823.
Cui, et al., "Targeted integration in rat and mouse embryos with zinc-finger nucleases," Nature Biotechnology, vol. 29, No. 1, 64-68 (Dec. 12, 2010).
Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.
Ding et al., "Enhanced Efficiency of Human Pluripotent Stem Cell Genome Editing through Replacing TALENs with CRISPRs," Cell Stem Cell, vol. 12, pp. 393-394 plus supplemental materials, 2013 (Apr. 4, 2013).
Ding, et al., "A Talen genome-editing system for generating human stem cell-based disease models," Cell Stem Cell, 2013, vol. 12, pp. 238-251.
Donoho et al., "Analysis of Gene Targeting and Intrachromosomal Homologous Recombination Stimulated by Genomic Double-Strand Breaks in Mouse Embryonic Stem Cells," Mol. Cell. Biol., vol. 18(7), pp. 4070-4078, 1998.
Doudna et al., "The new frontier of genome engineering with CRISPR-Cas9," Science, vol. 346(6213), pp. 1258096-1-1258096-9, Nov. 28, 2014.
Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.
Flisikowska, et al., "Efficient Immunoglobulin Gene Disruption and Targeted Replacement in Rabbit Using Zinc Finger Nucleases," Plos one, vol. 6 Issue 6 (Jun. 2011).
Fu, et al., "High-frequency off-target mutagenesis induced by CRISPR-Cas nucleases in human cells," Nature Biotechnology, 2013, vol. 31(9), pp. 822-826.
Fujii et al., "Efficient generation of genome-modified mice via offset-nicking by CRISPR/Cas system," Biochemical and Biophysical Research Communications, vol. 445(4), pp. 791-794 plus Supplementary Information, Jan. 31, 2014.
Garg, A., et al., "Engineering synthetic TAL effectors with orthogonal target sites," Nucleic Acids Research (2012), vol. 40(15), p. 7584-7595.
Gasiunas, G., et al., "Cas9-crRNA ribonucleoprotein complex mediates specific DNA cleavage for adaptive immunity in bacteria," PNAS, 2012, vol. 108, pp. 10098-10103.
Gibson, D., et al., "Enzymatic assembly of DNA molecules up to several hundred kilobases," Nature Methods, 2009, vol. 6(5), pp. 343-345.
Gibson, Daniel G., "Enzymatic Assembly of Overlapping DNA Fragments," Methods in Enzymology, 2011, vol. 498, pp. 349-361.
Gratz et al., "Genome Engineering of *Drosophila* with the CRISPR RNA-Guided Cas9 Nuclease," Genetics, vol. 194, pp. 1029-1035, 2013. (published May 2013).
Gratz et al., "Highly Specific and Efficient CRISPR/Cas9-Catalyzed Homology-Directed Repair in *Drosophila*," Genetics, vol. 196(4), pp. 961-971 plus Supporting Information, Jan. 29, 2014.
Horvath, P., et al., "CRISPR/Cas, the Immune System of Bacteria and Archaea," Science, 2010, vol. 327, pp. 167-170.
Hsu, et al., "DNA targeting specificity of RNA-guided Cas9 nucleases," Nature Biotechnology, 2013, vol. 31(9), pp. 827-832.
Hsu, P.D., et al., "Development and Applications of CRISPR-Cas9 for Genome Engineering," Cell (2014), vol. 157, pp. 1262-1278.
Hwang et al., "Efficient In Vivo Genome Editing Using RNA-Guided Nucleases," Nat. Biotechnol., vol. 31(3), pp. 227-229 (plus supplemental materials), 2013.
Jallepalli et al., "Securin is required for chromosomal stability in human cells," Cell, vol. 105(4), pp. 445-457, May 18, 2001.
Jiang, et al., "RNA-guided editing of bacterial genomes using CRISPR-Cas systems," Nature Biotechnology, 2013, vol. 31(3), pp. 233-239.

Jinek, M., et al., "A Programmable Dual-RNA-Guided DNA Endonuclease in Adaptive Bacterial Immunity," Science, 2012, vol. 337, pp. 816-821 plus Supplemental Materials, Jun. 28, 2012.
Jinek, M., et al., "A Programmable Dual-RNA-Guided DNA Endonuclease in Adaptive Bacterial Immunity," Science, 2012, vol. 337, pp. 816-821.
Johnson, et al., "A rapid assay to quantify the cleavage efficiency of custom-designed nucleases in planta," Plant Mol Biol, 82:207-221 (2013).
Kashimada et al., "Sry: the master switch in mammalian sex determination," Development, vol. 137(23), pp. 3921-3930, Dec. 2, 2010.
Kato et al., "Production of Sry knockout mouse using TALEN via oocyte injection," Scientific Reports, vol. 3, p. 3136, 2013 (published Nov. 5, 2013).
Kim et al., "Targeted genome editing in human cells with zinc finger nucleases constructed via modular assembly," Genome Res., vol. 19(7), pp. 1279-1288, 2009.
Kuno et al., "Generation of fertile and fecund F0 XY female mice from XY ES cells," Transgenic Research, vol. 24(1), pp. 19-29, 2014 (epub Aug. 3, 2014).
Kuroiwa, et al., "Sequential targeting of the genes encoding immunoglobulin-μ and prion protein in cattle," Nature Genetics, vol. 36, No. 7, (Jul. 2004).
Li et al., "Germline Competent Embryonic Stem Cells Derived from Rat Blastocysts," Cell, vol. 135, pp. 1299-1310, 2008.
Li et al., "Optimization of Genome Engineering Approaches with the CRISPR/Cas9 System," PLoS One, vol. 9(8), p. e105779, Aug. 28, 2014.
Li, D., et al., "Heritable gene targeting in the mouse and rat using a CRISPR-Cas system," Nature Biotechnology, 2013, vol. 31(8), pp. 681-683.
Li, et al., "Modularly assembled designer TAL effector nucleases for targeted gene knockout and gene replacement in eukaryotes," Nucleic Acids Research, 2011, vol. 39(14), pp. 6315-6325.
Liu et al., "A one-step cloning method for the construction of somatic cell gene targeting vectors: application to production of human knockout cell lines," BMC Biotechnol., vol. 12, p. 71, Oct. 9, 2012.
Lombardo, et al., "Gene editing in human stem cells using zinc finger nucleases and integrase-defective lentiviral vector delivery," Nature Biotechnology, 2007, vol. 25(11), pp. 1298-1306.
MacDonald, et al., "Precise and in situ genetic humanization of 6 Mb of mouse immunoglobulin genes," PNAS, vol. 111, No. 14: 5147-5152, (Apr. 8, 2014).
Mali et al., "RNA-Guided Human Genome Engineering via Cas9," Science, vol. 339(6121), pp. 823-826 plus Supplemental Materials, Jan. 3, 2013.
Mali et al., "CAS9 transcriptional activators for target specificity screening and paired nickases for cooperative genome engineering," Nature Biotechnology, vol. 31(9), pp. 833-838 plus Supplementary Information, Aug. 1, 2013.
Mali, et al., "Cas9 as a versatile tool for engineering biology," Nature Methods, vol. 10(10), pp. 957-963, 2013.
Mali, et al., "CAS9 transcriptional activators for target specificity screening and paired nickases for cooperative genome engineering," Nature Biotechnology, 2013, vol. 31(9), pp. 833-838.
Mali, et al., "RNA-guided human genome engineering via Cas9," Science, 2013, vol. 339(6121), pp. 823-826.
Manjunath., et al., "Newer Gene Editing Technologies toward HIV Gene Therapy," Viruses (2013), vol. 5, pp. 2748-2766.
Mashimo et al., "Generation of knockout rats with X-linked severe combined immunodeficiency (X-SCID) using zinc finger nucleases," PLoS One, vol. 5(1), p. e8870, 2010.
Meyer, et al., "Gene targeting by homologous recombination in mouse zygotes mediation by zinc-finger nucleases," PNAS, vol. 107, No. 24, pp. 105022-105026 (Aug. 24, 2010).
Miller, et al., "A TALE nuclease architecture for efficient genome editing," Nature Biotechnology, 2011, vol. 29(2), pp. 143-148.
Moehle et al., "Targeted gene addition into a specified location in the human genome using designed zinc finger nucleases," Proc. Natl. Acad. Sci. U.S.A., vol. 104(9), pp. 3055-3060, 2007 (epub Feb. 20, 2007).

(56) References Cited

OTHER PUBLICATIONS

Moscou and Bogdanove, "A simple cipher governs DNA recognition by TAL effectors," Science, 2009, vol. 326, p. 1501.
Mussolino, et al., "TALE nucleases: tailored genome engineering made easy," Curr. Opin. Biotechnol., vol. 23(5), pp. 644-650, 2012. (epub Feb. 17, 2012).
Narsinh, et al., "Gene Correction in Human Embryonic and Induced Pluripotent Stem Cells: Promise and Challenges Ahead", Molecular Therapy, vol. 18, No. 6, pp. 1061-1063, (Jun. 2010).
News Feature "Move over ZFNs," Nature Biotechnology, 2011, vol. 29(8), pp. 681-684.
Pabo, et al., "Design and Selection of Novel Cys2His2 Zinc Finger Proteins," Annu. Rev. Biochem., 70:313-341, (2001).
Pattanayak, et al., "High-throughput profiling of off-target DNA cleavage reveals RNA-programmed Cas9 nuclease specificity," Nature Biotechnology, 2013, vol. 31(9), pp. 839-843.
PCT International Preliminary Report on Patentability for application PCT/US2013/038165 dated Oct. 28, 2014.
PCT International Preliminary Report on Patentability for application PCT/US2014/034412 dated Oct. 30, 2015.
PCT International Search Report and Written Opinion of the International Searching Authority for application PCT/US2014/060788 dated Jan. 26, 2015.
PCT International Search Report for application PCT/US2015/034503 dated Sep. 8, 2015.
PCT Written Opinion of the International Searching Authority for application PCT/US2015/034503 dated Sep. 8, 2015.
PCT/US2013/038165 International Search Report and Written Opinion dated Jul. 12, 2013.
PCT/US2014/034412 International Search Report and Written Opinion of the Searching Authority dated Oct. 9, 2014.
PCT/US2015/038001 Invitation of Pay Additional Fees dated Nov. 13, 2015.
PCT/US2015/062023 Invitation of Pay Additional Fees dated Feb. 8, 2016.
Pennisi, E., "Beyond TALENs," Science (2012), vol. 338, p. 1411.
Perez et al., "Establishment of HIV-1 resistance in CD4+ T cells by genome editing using zinc finger nucleases," Nature Biotech., vol. 26(7), pp. 808-816, 2008.
Perez-Pinera, et al., "Gene targeting to the ROSA26 locus directed by engineered zinc finger nucleases," Nucleic Acids Research, vol. 40, No. 8, pp. 3741-3752 (2011).
Porteus, et al,, "Gene targeting using zinc finger nucleases," Nature Biotechnology, vol. 23(8), pp. 967-973, 2005.
Poueymirou et al., "F0 generaton mice fully derived from gene-targeted embryonic stem cells allowing immediate analysis," Nature Biotechnology, Epub Dec. 24, 2006, vol. 25(1):91-99.
Qi, et al., "Repurposing CRISPR as an RNA-guided platform for sequence-specific control of gene expression," Cell, 2013, vol. 152, pp. 1173-1183.
Ramirez et al., "Engineered zinc finger nickases induce homology-directed repair with reduced mutagenic effects," Nucleic Acids Research, vol. 40(12), pp. 5560-5568, 2012. (published Feb. 2012).
Ran et al., "Double nicking by RNA-guided CRISPR Cas9 for enhanced genome editing specificity," Cell, vol. 154, pp. 1380-1389, 2013.
Schwank, G., et al., "Functional Repair of CFTR by CRISPR/Cas9 in Intestinal Stem Cell Organoids of Cystic Fibrosis Patients," Cell Stem Cell (2013), vol. 13, pp. 653-658.
Shan et al., "Targeted genome modification of crop plants using a CRISPR-Cas system," Nature Biotechnology, vol. 31(8), pp. 686-688, Aug. 1, 2013.
Sharan, et al., "Recombineering: A Homologous Recombination-Based Method of Genetic Engineering," Nat Protoc., 4(2): 206-223, (2009).
Stemgent Product Specification Sheet, PD0325901, pp. 1-2 (2012).
Tong et al., "Generating gene knockout rats by homologous recombination in embryonic stem cells," Nature Protocols, vol. 6(6), pp. 827-844, 2011 (epub May 26, 2011).
U.S. Appl. No. 13/870,280 Final Rejection dated Oct. 15, 2015.
U.S. Appl. No. 13/870,280 Non-Final Office Action dated Jan. 3, 2017.
U.S. Appl. No. 13/870,280, Notice of Allowance dated Jun. 12, 2017.
U.S. Appl. No. 13/870,280, Notice of Allowance dated Sep. 19, 2017.
U.S. Appl. No. 13/870,280, Requirement for Restriction/Election dated Jul. 22, 2014.
U.S. Appl. No. 14/254,715 Final Office Action dated Nov. 30, 2015.
U.S. Appl. No. 14/254,715, Non-Final Office Action dated Aug. 12, 2015.
U.S. Appl. No. 14/314,866, Advisory Action dated Aug. 12, 2015.
U.S. Appl. No. 14/314,866, Non-Final Office Action dated Dec. 26, 2014.
U.S. Appl. No. 14/314,866, Non-Final Office Action dated Nov. 27, 2015.
U.S. Appl. No. 14/314.866, Final Office Action dated Jun. 4, 2015.
U.S. Appl. No. 14/578,291, Non-Final Office Action dated Mar. 10, 2015.
U.S. Appl. No. 14/578,291, Notice of Allowance dated Aug. 26, 2015.
U.S. Appl. No. 14/731,914 , Requirement for Restriction/Election dated Dec. 31, 2015.
U.S. Appl. No. 13/870,280 , Advisory Action dated Jan. 5, 2016.
U.S. Appl. No. 13/870,280, Non-Final Office Action dated Mar. 13, 2015.
U.S. Appl. No. 14/254,715, Requirement for Restriction/Election dated Jun. 4, 2015.
U.S. Appl. No. 14/928,180, Non-Final Office Action dated Jan. 5, 2016.
Urnov, et al., "Highly efficient endogenous human gene correction using designed zinc-finger nucleases," Nature, vol. 435 (Jun. 2005).
Valenzuela, D. M. et al., "High-throughput engineering of the mouse genome coupled with high-resolution expression analysis", Nature Biotechnology, (2003), vol. 21, No. 6, pp. 652-659.
Van Der Oost, "New tool for genome surgery," Science, 2013, vol. 339(6121), pp. 768-770.
Wang et al., "One-Step Generation of Mice Carrying Mutations in Multiple Genes by CRISPR/Cas-Mediated Genome Engineering," Cell, vol. 153, pp. 910-918, 2013. (published May 2013).
Wang et al., "Talen-mediated editing of the mouse Y chromosome," Nature Biotechnology, vol. 31(6), p. 530-532, 2013 (epub May 12, 2013).
Wang, H., et al., "One-Step Generation of Mice Carrying Mutations in Multiple Genes by CRISPR/Cas-Mediated Genome Engineering," Cell, 2013, vol. 153(4), pp. 910-918.
Wen et al., "Completely ES Cell-Derived Mice Produced by Tetraploid Complementation Using Inner Cell Mass (ICM) Deficient Blastocysts," PLoS One, Vol. 9(4), e94730, Apr. 14, 2014.
Whitworth et al., "Use of the CRISPR/Cas9 System to Produce Genetically Engineered Pigs from In Vitro-Derived Oocytes and Embryos," Biology of Reproduction, Vol. 91(3), p. 78, Aug. 6, 2014.
Yoshimi et al., "Allele-specific genome editing and correction of disease-associated phenotypes in rats using the CRISPR-Cas platform," Nature Communications, vol. 5, p. 4240 plus Supplementary Information, Jun. 26, 2014.
Zhang et al., "Biallelic targeting of expressed genes in mouse embryonic stem cells using the Cas9 system," Methods, vol. 69(2), pp. 171-178, Jun. 12, 2014.

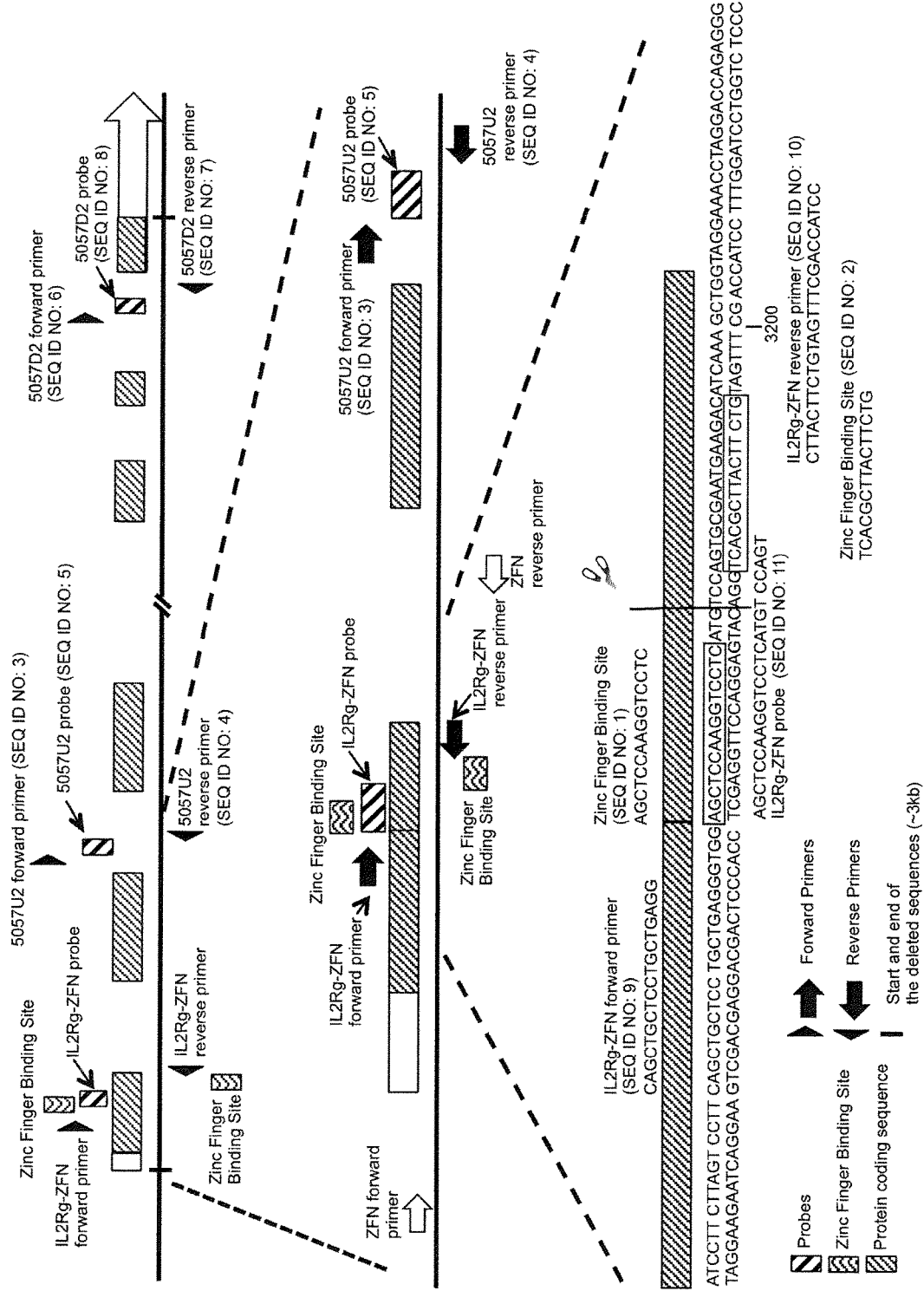

NUCLEASE-MEDIATED TARGETING WITH LARGE TARGETING VECTORS

CROSS REFERENCE TO RELATED APPLICATIONS

This application is a continuing application of U.S. application Ser. No. 13/870,280 filed Apr. 25, 2013, which claims priority to U.S. Application No. 61/638,267 filed Apr. 25, 2012, each of which is herein incorporated by reference in its entirety.

REFERENCE TO A SEQUENCE LISTING SUBMITTED AS A TEXT FILE VIA EFS WEB

The Sequence Listing written in file 501234SEQLIST.txt is 2.14 kilobytes, was created on Oct. 23, 2017, and is hereby incorporated by reference.

FIELD

Nucleases and DNA constructs, including targeting vectors (e.g., large targeting vectors, "LTVEC") for achieving homologous recombination at a target genomic locus. Compositions and methods for making a targeted genetic modification via homologous recombination that is facilitated by a single or double-strand break at or near a target genomic locus. Compositions and methods for promoting efficiency of homologous recombination between an LTVEC and a target genomic locus in prokaryotic or eukaryotic cells employing engineered nucleases.

BACKGROUND

Homologous recombination using targeting vectors that are specifically designed to add, delete, or replace a particular nucleic acid sequence at a genomic locus is a popular approach to achieving a desired genomic modification in non-human animals. A nuclease that is specifically engineered to introduce a singe or a double-strand break at or near a target genomic locus can be used together with a targeting vector to enhance efficiency of homologous recombination at the target genomic locus.

Although the art of genome modification through homologous recombination has advanced considerably over the last two decades, difficulties still remain with achieving an acceptable targeting frequency using very large targeting vectors, LTVECs, in many circumstances, for example, when a large portion of a rodent genome is replaced with a large human genomic fragment, or difficulties targeting certain cell types, e.g., fibroblasts or other somatic cells. There is a need in the art for further and improved methods for modifying large genomic loci of a eukaryotic genome using LTVECs.

SUMMARY

Compositions and methods are provided for modifying a genomic locus of interest using a large targeting vector (LTVEC) in combination with a nuclease agent, which allow efficient deletion, addition (e.g., insertion), and/or replacement of a large nucleic acid sequence at the genomic locus of interest.

Compositions and methods are provided for modifying a target genomic locus of a mammal in a prokaryotic cell using an LTVEC and a nuclease agent via bacterial homologous recombination (BHR), wherein the BHR is facilitated by a single or double-strand cleavage at or near the target genomic locus created by the nuclease agent. Prokaryotic cells are provided comprising an LTVEC and a nuclease agent that, upon expression, is capable of introducing a single or double-strand cleavage at or near a target site. Compositions and methods are provided for replacing a large genomic locus of a non-human animal with an exogenous nucleic acid sequence, e.g., homologous or orthologous human genomic nucleic acid sequences, in a recombinogenic prokaryotic cell by employing various LTVECs and nucleases as described herein.

Compositions and methods are provided for modifying a genomic locus of interest using an LTVEC and a nuclease agent in various pluripotent mammalian cells. Compositions and methods are provided for replacing a large genomic locus of a non-human animal with exogenous nucleic acid sequence, e.g., homologous or orthologous human genomic nucleic acid sequences, in a pluripotent cell of the non-human animal by employing various LTVECs and nucleases as described herein.

Pluripotent cells of a non-human animal are provided comprising various LTVECs and nuclease agents described herein.

Compositions and methods are provided for generating a genetically modified non-human animal comprising one or more targeted genetic modifications as described herein.

In one aspect, a prokaryotic cell is provided, comprising a large targeting vector (LTVEC) comprising homology arms directed to a target locus, and a nucleic acid sequence encoding a nuclease agent that makes a single- or double-strand break at or near the target locus.

In one embodiment, the prokaryotic cell is capable of expressing a recombinase that mediates bacterial homologous recombination (BHR). In one embodiment, the prokaryotic cell is a recombination-competent strain of E. coli.

In one embodiment, the LTVEC ranges from about 50 kb to about 300 kb. In one embodiment, the LTVEC ranges from about 50 kb to about 75 kb. In one embodiment, the LTVEC ranges from about 75 kb to about 100 kb. In one embodiment, the LTVEC ranges from about 100 kb to 125 kb. In one embodiment, the LTVEC ranges from about 125 kb to about 150 kb. In one embodiment, the LTVEC ranges from about 150 kb to about 175 kb. In one embodiment, the LTVEC ranges from about 175 kb to about 200 kb. In one embodiment, the LTVEC ranges from about 200 kb to about 225 kb. In one embodiment, the LTVEC ranges from about 225 kb to about 250 kb. In one embodiment, the LTVEC ranges from about 250 kb to about 275 kb. In one embodiment, the LTVEC ranges from about 275 kb to about 300 kb.

In one embodiment, the homology arms of the targeting vector are derived from a BAC library, a cosmid library, or a P1 phage library. In one embodiment, the homology arms are derived from a genomic locus of the non-human animal that is not targetable using a conventional method. In one embodiment, the homology arms are derived from a synthetic DNA.

In one embodiment, a sum total of the upstream homology arm and the downstream homology arm is at least 10 kb. In one embodiment, the upstream homology arm ranges from about 5 kb to about 100 kb. In one embodiment, the downstream homology arm ranges from about 5 kb to about 100 kb. In one embodiment, the upstream and the downstream homology arms range from about 5 kb to about 10 kb. In one embodiment, the upstream and the downstream homology arms range from about 10 kb to about 20 kb. In one embodiment, the upstream and the downstream homology arms range from about 20 kb to about 30 kb. In one embodiment, the upstream and the downstream homology arms range from about 30 kb to about 40 kb. In one embodiment, the upstream and the downstream homology arms range from about 40 kb to about 50 kb. In one embodiment, the upstream and the downstream homology arms range from about 50 kb to about 60 kb. In one embodiment, the upstream and the downstream homology arms range from about 60 kb to about 70 kb. In one embodiment, the upstream and the downstream homology arms range from about 70 kb to about 80 kb. In one embodiment, the upstream and the downstream homology arms range from about 80 kb to about 90 kb. In one embodiment, the upstream and the downstream homology arms range from about 90 kb to about 100 kb. In one embodiment, the upstream and the downstream homology arms range from about 100 kb to about 110 kb. In one embodiment, the upstream and the downstream homology arms range from about 110 kb to about 120 kb. In one embodiment, the upstream and the downstream homology arms range from about 120 kb to about 130 kb. In one embodiment, the upstream and the downstream homology arms range from about 130 kb to about 140 kb. In one embodiment, the upstream and the downstream homology arms range from about 140 kb to about 150 kb. In one embodiment, the upstream and the downstream homology arms range from about 150 kb to about 160 kb. In one embodiment, the upstream and the downstream homology arms range from about 160 kb to about 170 kb. In one embodiment, the upstream and the downstream homology arms range from about 170 kb to about 180 kb. In one embodiment, the upstream and the downstream homology arms range from about 180 kb to about 190 kb. In one embodiment, the upstream and the downstream homology arms range from about 190 kb to about 200 kb.

In one embodiment, the LTVEC comprises a selection cassette. In one embodiment, the selection cassette comprises a nucleic acid sequence encoding a selection marker, wherein the nucleic acid sequence is operably linked to a promoter. In one embodiment, the promoter is active in a prokaryotic cell. In one embodiment, the promoter is active both in prokaryotic and eukaryotic cells. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof.

In one embodiment, the LTVEC comprises an insert nucleic acid ranging from about 5 kb to about 200 kb. In one embodiment, the insert nucleic acid is from about 5 kb to about 10 kb. In one embodiment, the insert nucleic acid is from about 10 kb to about 20 kb. In one embodiment, the insert nucleic acid is from about 20 kb to about 30 kb. In one embodiment, the insert nucleic acid is from about 30 kb to about 40 kb. In one embodiment, the insert nucleic acid is from about 40 kb to about 50 kb. In one embodiment, the insert nucleic acid is from about 60 kb to about 70 kb. In one embodiment, the insert nucleic acid is from about 80 kb to about 90 kb. In one embodiment, the insert nucleic acid is from about 90 kb to about 100 kb. In one embodiment, the insert nucleic acid is from about 100 kb to about 110 kb. In one embodiment, the insert nucleic acid is from about 120 kb to about 130 kb. In one embodiment, the insert nucleic acid is from about 130 kb to about 140 kb. In one embodiment, the insert nucleic acid is from about 140 kb to about 150 kb. In one embodiment, the insert nucleic acid is from about 150 kb to about 160 kb. In one embodiment, the insert nucleic acid is from about 160 kb to about 170 kb. In one embodiment, the insert nucleic acid is from about 170 kb to about 180 kb. In one embodiment, the insert nucleic acid is from about 180 kb to about 190 kb. In one embodiment, the insert nucleic acid is from about 190 kb to about 200 kb.

In one embodiment, the LTVEC comprises an insert nucleic acid comprising a nucleic acid flanked with site-specific recombination target sequences. In one embodiment, the nucleic acid comprises a genomic nucleic acid. In one embodiment, the genomic nucleic acid is derived from a mouse, a human, or a combination thereof. In one embodiment, the site-specific recombination target sequences are selected from the group consisting of loxP, lox511, lox2272, lox66, lox71, loxM2, lox5171, FRT, FRT11, FRT71, attp, att, FRT, rox, and a combination thereof.

In one embodiment, the LTVEC comprises an insert nucleic acid comprising a conditional allele. In one embodiment, the conditional allele is a multifunctional allele, as described in US 2011/0104799, which is incorporated by reference in its entirety. In one embodiment, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

In one embodiment, the LTVEC comprises an insert nucleic acid comprising a selection cassette. In one embodiment, the selection cassette comprises a nucleic acid sequence encoding a selection marker, wherein the nucleic acid sequence is operably linked to a promoter. In one embodiment, the promoter is active in a prokaryotic cell. In one embodiment, the nucleic acid is active in both prokaryotic and eukaryotic cells. In one embodiment, the selection cassette is flanked with site-specific recombination target sequences. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/ guanine phosphoribosyl transferase (gpt), and herpes simplex virus thymidine kinase (HSV-k), and a combination thereof.

In one embodiment, the LTVEC comprises an insert nucleic acid comprising a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. In one embodiment, the reporter gene is expressed under a control of an inducible promoter. In one embodiment, the reporter gene is expressed under a control of an endogenous promoter. In one embodiment, the reporter gene is expressed under a control of an exogenous promoter. In one embodiment, the reporter gene is expressed in a specific cell type. In one embodiment, the reporter gene is expressed in a tissue-specific manner. In one embodiment, the reporter gene is expressed in a developmental stage-specific manner.

In one aspect, a eukaryotic cell is provided, comprising a large targeting vector comprising homology arms directed to a target locus within the genome of the eukaryotic cell, and a nucleic acid sequence encoding a nuclease agent that makes a single- or double-stranded break at or near the target locus.

In one embodiment, the eukaryotic cell is a pluripotent cell. In one embodiment, the pluripotent cell is an embryonic stem (ES) cell. In one embodiment, the pluripotent cell is a non-human ES cell. In one embodiment, the pluripotent cell is an induced pluripotent stem (iPS) cell. In one embodiment, the induced pluripotent (iPS) cell is derived from a fibroblast. In one embodiment, the induced pluripotent (iPS) cell is derived from a human fibroblast. In one embodiment, the pluripotent cell is a hematopoietic stem cell (HSC). In one embodiment, the pluripotent cell is a neuronal stem cell (NSC). In one embodiment, the pluripotent cell is an epiblast stem cell. In one embodiment, the pluripotent cell is a developmentally restricted progenitor cell. In one embodiment, the pluripotent cell is a rodent pluripotent cell. In one embodiment, the rodent pluripotent cell is a rat pluripotent cell. In one embodiment, the rat pluripotent cell is a rat ES cell. In one embodiment, the rodent pluripotent cell is a mouse pluripotent cell. In one embodiment, the pluripotent cell is a mouse embryonic stem (ES) cell.

In one embodiment, the eukaryotic cell is an immortalized mouse or rat cell. In one embodiment, the eukaryotic cell is an immortalized human cell. In one embodiment, the eukaryotic cell is a human fibroblast. In one embodiment, the eukaryotic cell is a cancer cell. In one embodiment, the eukaryotic cell is a human cancer cell.

In one embodiment, the LTVEC ranges from about 50 kb to about 300 kb. In one embodiment, the LTVEC ranges from about 50 kb to about 75 kb. In one embodiment, the LTVEC ranges from about 75 kb to about 100 kb. In one embodiment, the LTVEC ranges from about 100 kb to 125 kb. In one embodiment, the LTVEC ranges from about 125 kb to about 150 kb. In one embodiment, the LTVEC ranges from about 150 kb to about 175 kb. In one embodiment, the LTVEC ranges from about 175 kb to about 200 kb. In one embodiment, the LTVEC ranges from about 200 kb to about 225 kb. In one embodiment, the LTVEC ranges from about 225 kb to about 250 kb. In one embodiment, the LTVEC ranges from about 250 kb to about 275 kb. In one embodiment, the LTVEC ranges from about 275 kb to about 300 kb.

In one embodiment, the homology arms of the targeting vector are derived from a BAC library, a cosmid library, or a P1 phage library. In one embodiment, the homology arms are derived from a genomic locus of the non-human animal that is not targetable using a conventional method. In one embodiment, the homology arms are derived from a synthetic DNA.

In one embodiment, a sum total of the upstream homology arm and the downstream homology arm is at least 10 kb. In one embodiment, the upstream homology arm ranges from about 5 kb to about 100 kb. In one embodiment, the downstream homology arm ranges from about 5 kb to about 100 kb. In one embodiment, the upstream and the downstream homology arms range from about 5 kb to about 10 kb. In one embodiment, the upstream and the downstream homology arms range from about 10 kb to about 20 kb. In one embodiment, the upstream and the downstream homology arms range from about 20 kb to about 30 kb. In one embodiment, the upstream and the downstream homology arms range from about 30 kb to about 40 kb. In one embodiment, the upstream and the downstream homology arms range from about 40 kb to about 50 kb. In one embodiment, the upstream and the downstream homology arms range from about 50 kb to about 60 kb. In one embodiment, the upstream and the downstream homology arms range from about 60 kb to about 70 kb. In one embodiment, the upstream and the downstream homology arms range from about 70 kb to about 80 kb. In one embodiment, the upstream and the downstream homology arms range from about 80 kb to about 90 kb. In one embodiment, the upstream and the downstream homology arms range from about 90 kb to about 100 kb. In one embodiment, the upstream and the downstream homology arms range from about 100 kb to about 110 kb. In one embodiment, the upstream and the downstream homology arms range from about 110 kb to about 120 kb. In one embodiment, the upstream and the downstream homology arms range from about 120 kb to about 130 kb. In one embodiment, the upstream and the downstream homology arms range from about 130 kb to about 140 kb. In one embodiment, the upstream and the downstream homology arms range from about 140 kb to about 150 kb. In one embodiment, the upstream and the downstream homology arms range from about 150 kb to about 160 kb. In one embodiment, the upstream and the downstream homology arms range from about 160 kb to about 170 kb. In one embodiment, the upstream and the downstream homology arms range from about 170 kb to about 180 kb. In one embodiment, the upstream and the downstream homology arms range from about 180 kb to about 190 kb. In one embodiment, the upstream and the downstream homology arms range from about 190 kb to about 200 kb.

In one embodiment, the LTVEC comprises a selection cassette. In one embodiment, the selection cassette comprises a nucleic acid sequence encoding a selection marker, wherein the nucleic acid sequence is operably linked to a promoter. In one embodiment, the promoter is active in a prokaryotic cell. In one embodiment, the promoter is active both in prokaryotic and eukaryotic cells. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof.

In one embodiment, the LTVEC comprises an insert nucleic acid ranging from about 5 kb to about 200 kb. In one embodiment, the insert nucleic acid is from about 5 kb to about 10 kb. In one embodiment, the insert nucleic acid is from about 10 kb to about 20 kb. In one embodiment, the insert nucleic acid is from about 20 kb to about 30 kb. In one embodiment, the insert nucleic acid is from about 30 kb to about 40 kb. In one embodiment, the insert nucleic acid is from about 40 kb to about 50 kb. In one embodiment, the insert nucleic acid is from about 60 kb to about 70 kb. In one embodiment, the insert nucleic acid is from about 80 kb to about 90 kb. In one embodiment, the insert nucleic acid is from about 90 kb to about 100 kb. In one embodiment, the insert nucleic acid is from about 100 kb to about 110 kb. In one embodiment, the insert nucleic acid is from about 120 kb to about 130 kb. In one embodiment, the insert nucleic acid is from about 130 kb to about 140 kb. In one embodiment, the insert nucleic acid is from about 140 kb to about 150 kb. In one embodiment, the insert nucleic acid is from about 150 kb to about 160 kb. In one embodiment, the insert nucleic acid is from about 160 kb to about 170 kb. In one embodiment, the insert nucleic acid is from about 170 kb to about 180 kb. In one embodiment, the insert nucleic acid is from about 180 kb to about 190 kb. In one embodiment, the insert nucleic acid is from about 190 kb to about 200 kb.

In one embodiment, the LTVEC comprises an insert nucleic acid comprising a nucleic acid flanked with site-specific recombination target sequences. In one embodiment, the nucleic acid comprises a genomic nucleic acid. In one embodiment, the genomic nucleic acid is derived from a mouse, a human, or a combination thereof. In one embodiment, the site-specific recombination target sequences are selected from the group consisting of loxP, lox511, lox2272, lox66, lox71, loxM2, lox5171, FRT, FRT11, FRT71, attp, att, FRT, rox, and a combination thereof.

In one embodiment, the LTVEC comprises an insert nucleic acid comprising a conditional allele. In one embodiment, the conditional allele is a multifunctional allele, as described in US 2011/0104799, which is incorporated by reference in its entirety. In one embodiment, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

In one embodiment, the LTVEC comprises an insert nucleic acid comprising a selection cassette. In one embodiment, the selection cassette comprises a nucleic acid sequence encoding a selection marker, wherein the nucleic acid sequence is operably linked to a promoter. In one embodiment, the promoter is active in a prokaryotic cell. In one embodiment, the nucleic acid is active in both prokaryotic and eukaryotic cells. In one embodiment, the selection cassette is flanked with site-specific recombination target sequences. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof.

In one embodiment, the LTVEC comprises an insert nucleic acid comprising a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. In one embodiment, the reporter gene is expressed under a control of an inducible promoter. In one embodiment, the reporter gene is expressed under a control of an endogenous promoter. In one embodiment, the reporter gene is expressed under a control of an exogenous promoter. In one embodiment, the reporter gene is expressed in a specific cell type. In one embodiment, the reporter gene is expressed in a tissue-specific manner. In one embodiment, the reporter gene is expressed in a developmental stage-specific manner.

In one aspect, a method for modifying a target genomic locus of a mammalian cell via bacterial homologous recombination (BHR) in a prokaryotic cell is provided, comprising:
(a) introducing into a prokaryotic cell comprising a target genomic locus of a mammal:
(i) a targeting vector comprising an insert nucleic acid flanked with a first upstream homology arm and a first downstream homology arm, and
(ii) a nuclease agent that makes a single or double-strand break at or near the target genomic locus, and
(i) selecting a targeted prokaryotic cell comprising the insert nucleic acid,
wherein the prokaryotic cell is capable of expressing a recombinase that mediates the BHR.

In one embodiment, the target genomic locus is selected from an FcER1a locus, a TLR4 locus, a PRLR locus, a Notch4 locus, an Accn2 locus, an Adamts5 locus, a TRPA1 locus, FolH1 locus, an LRP5 locus, and an ERBB4 locus.

In one embodiment, the target genomic locus is present in a large targeting vector (LTVEC) comprising a second upstream homology arm and a second downstream homology arm. In one embodiment, a sum total of the second upstream homology arm and the second downstream homology arm is at least 10 kb. In one embodiment, the second upstream homology arm ranges from about 5 kb to about 100 kb. In one embodiment, the second downstream homology arm ranges from about 5 kb to about 100 kb. In one embodiment, the second upstream and the downstream homology arms range from about 5 kb to about 10 kb. In one embodiment, the second upstream and the downstream homology arms range from about 10 kb to about 20 kb. In one embodiment, the second upstream and the downstream homology arms range from about 20 kb to about 30 kb. In one embodiment, the second upstream and the downstream homology arms range from about 30 kb to about 40 kb. In one embodiment, the second upstream and the downstream homology arms range from about 40 kb to about 50 kb. In one embodiment, the second upstream and the downstream homology arms range from about 50 kb to about 60 kb. In one embodiment, the second upstream and the downstream homology arms range from about 60 kb to about 70 kb. In one embodiment, the second upstream and the downstream homology arms range from about 70 kb to about 80 kb. In one embodiment, the second upstream and the downstream homology arms range from about 80 kb to about 90 kb. In one embodiment, the second upstream and the downstream homology arms range from about 90 kb to about 100 kb. In one embodiment, the second upstream and the downstream homology arms range from about 100 kb to about 110 kb. In one embodiment, the second upstream and the downstream homology arms range from about 110 kb to about 120 kb. In one embodiment, the second upstream and the downstream homology arms range from about 120 kb to about 130 kb. In one embodiment, the second upstream and the downstream homology arms range from about 130 kb to about 140 kb. In one embodiment, the second upstream and the downstream homology arms range from about 140 kb to about 150 kb. In one embodiment, the second upstream and the downstream homology arms range from about 150 kb to about 160 kb. In one embodiment, the second upstream and the downstream homology arms range from about 160 kb to about 170 kb. In one embodiment, the second upstream and the downstream homology arms range from about 170 kb to about 180 kb. In one embodiment, the second upstream and the downstream homology arms range from about 180 kb to about 190 kb. In one embodiment, the second upstream and the downstream homology arms range from about 190 kb to about 200 kb.

In one embodiment, the mammal is a human and the targeting is of an ex vivo human cell. In one embodiment, the mammal is a rodent. In one embodiment, the rodent is selected from a mouse, a rat, and a hamster.

In one embodiment, the nuclease agent is introduced together with the targeting vector. In one embodiment, the nuclease agent is introduced separately from the targeting vector over a period of time. In one embodiment, the nuclease agent is introduced prior to the introduction of the targeting vector. In one embodiment, the nuclease agent is introduced following introduction of the targeting vector.

In one embodiment, combined use of the targeting vector with the nuclease agent results in an increased targeting efficiency compared to use of the targeting vector alone. In one embodiment, when the targeting vector is used in conjunction with the nuclease agent, targeting efficiency of the targeting vector is increased at least by two-fold compared to when the targeting vector is used alone. In one embodiment, when the targeting vector is used in conjunction with the nuclease agent, targeting efficiency of the targeting vector is increased at least by three-fold compared to when the targeting vector is used alone. In one embodiment, when the targeting vector is used in conjunction with the nuclease agent, targeting efficiency of the targeting vector is increased at least by four-fold compared to when the targeting vector is used alone.

In one embodiment, the prokaryotic cell is a recombination-competent strain of E. coli. In one embodiment, the prokaryotic cell comprises a nucleic acid that encodes the recombinase. In one embodiment, the prokaryotic cell does not comprise the nucleic acid that encodes the recombinase, and the nucleic acid encoding the recombinase is introduced into the prokaryotic cell. In one embodiment, the nucleic acid comprises a DNA or an mRNA encoding the recombinase. In one embodiment the nucleic acid encoding the recombinase is pABG. In one embodiment, the recombinase is expressed under the control of an inducible promoter. In one embodiment, expression of the recombinase is controlled by arabinose.

In one embodiment, the nuclease agent is an expression construct comprising a nucleic acid sequence encoding a nuclease, wherein the nucleic acid sequence is operably linked to a promoter. In one embodiment, the promoter is a constitutively active promoter. In one embodiment, the promoter is an inducible promoter. In one embodiment, the promoter is active in the prokaryotic cell. In one embodiment, the nuclease agent is an mRNA encoding an endonuclease.

In one embodiment, the nuclease agent is a zinc-finger nuclease (ZFN). In one embodiment, each monomer of the ZFN comprises 3 or more zinc finger-based DNA binding domains, wherein each zinc finger-based DNA binding domain binds to a 3 bp subsite. In one embodiment, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site, and wherein the FokI nucleases dimerize and make a double strand break.

In one embodiment, the nuclease agent is a Transcription Activator-Like Effector Nuclease (TALEN). In one embodiment, each monomer of the TALEN comprises 12-25 TAL repeats, wherein each TAL repeat binds a 1 bp subsite. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by about 6 bp to about 40 bp cleavage site, and wherein the FokI nucleases dimerize and make a double strand break at a target sequence.

In one embodiment, each monomer of the nuclease recognizes a target sequence of at least 9 nucleotides. In one embodiment, the target sequence is from about 9 to about 12 nucleotides in length. In one embodiment, the target sequence is from about 12 to about 15 nucleotides in length. In one embodiment, the target sequence is from about 15 to about 18 nucleotides in length. In one embodiment, the target sequence is from about 18 to about 21 nucleotides in length.

In one embodiment, a target sequence of the nuclease agent is located in an intron. In one embodiment, the target sequence is located in an exon. In one embodiment, the target sequence is located in a promoter. In one embodiment, the target sequence is in a non-protein-coding region. In one embodiment, the non-protein-coding region is a regulatory region. In one embodiment, the target sequence is located in a promoter regulatory region. In one embodiment, the target sequence is located in an enhancer region.

In one embodiment, the nuclease agent is a meganuclease. In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG family of homing nuclease. In one embodiment, the LAGLIDADG family of homing nuclease is selected from I-SceI, I-CreI, and I-DmoI.

In one embodiment, the targeting vector is a large targeting vector (LTVEC).

In one embodiment, the LTVEC ranges from about 50 kb to about 300 kb. In one embodiment, the LTVEC ranges from about 50 kb to about 75 kb. In one embodiment, the LTVEC ranges from about 75 kb to about 100 kb. In one embodiment, the LTVEC ranges from about 100 kb to 125 kb. In one embodiment, the LTVEC ranges from about 125 kb to about 150 kb. In one embodiment, the LTVEC ranges from about 150 kb to about 175 kb. In one embodiment, the LTVEC ranges from about 175 kb to about 200 kb. In one embodiment, the LTVEC ranges from about 200 kb to about 225 kb. In one embodiment, the LTVEC ranges from about 225 kb to about 250 kb. In one embodiment, the LTVEC ranges from about 250 kb to about 275 kb. In one embodiment, the LTVEC ranges from about 275 kb to about 300 kb.

In one embodiment, the homology arms of the targeting vector are derived from a BAC library, a cosmid library, or a P1 phage library. In one embodiment, the homology arms are derived from a genomic locus of the non-human animal that is not targetable using a conventional method. In one embodiment, the homology arms are derived from a synthetic DNA.

In one embodiment, a sum total of the upstream homology arm and the downstream homology arm is at least 10 kb. In one embodiment, the upstream homology arm ranges from about 5 kb to about 100 kb. In one embodiment, the downstream homology arm ranges from about 5 kb to about 100 kb. In one embodiment, the upstream and the downstream homology arms range from about 5 kb to about 10 kb. In one embodiment, the upstream and the downstream homology arms range from about 10 kb to about 20 kb. In one embodiment, the upstream and the downstream homology arms range from about 20 kb to about 30 kb. In one embodiment, the upstream and the downstream homology arms range from about 30 kb to about 40 kb. In one embodiment, the upstream and the downstream homology arms range from about 40 kb to about 50 kb. In one embodiment, the upstream and the downstream homology arms range from about 50 kb to about 60 kb. In one embodiment, the upstream and the downstream homology arms range from about 60 kb to about 70 kb. In one embodiment, the upstream and the downstream homology arms range from about 70 kb to about 80 kb. In one embodiment, the upstream and the downstream homology arms range from about 80 kb to about 90 kb. In one embodiment, the upstream and the downstream homology arms range from about 90 kb to about 100 kb. In one embodiment, the upstream and the downstream homology arms range from about 100 kb to about 110 kb. In one embodiment, the upstream and the downstream homology arms range from about 110 kb to about 120 kb. In one embodiment, the upstream and the downstream homology arms range from about 120 kb to about 130 kb. In one embodiment, the upstream and the downstream homology arms range from about 130 kb to about 140 kb. In one embodiment, the upstream and the downstream homology arms range from about 140 kb to about 150 kb. In one embodiment, the upstream and the downstream homology arms range from about 150 kb to about 160 kb. In one embodiment, the upstream and the downstream homology arms range from about 160 kb to about 170 kb. In one embodiment, the upstream and the downstream homology arms range from about 170 kb to about 180 kb. In one embodiment, the upstream and the downstream homology arms range from about 180 kb to about 190 kb. In one embodiment, the upstream and the downstream homology arms range from about 190 kb to about 200 kb.

In one embodiment, the targeting vector comprises a selection cassette. In one embodiment, the selection cassette comprises a nucleic acid sequence encoding a selection marker, wherein the nucleic acid sequence is operably linked to a promoter. In one embodiment, the promoter is active in a prokaryotic cell. In one embodiment, the promoter is active both in prokaryotic and eukaryotic cells. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof.

In one embodiment, the insert nucleic acid is from about 5 kb to about 200 kb. In one embodiment, the insert nucleic acid is from about 5 kb to about 10 kb. In one embodiment, the insert nucleic acid is from about 10 kb to about 20 kb. In one embodiment, the insert nucleic acid is from about 20 kb to about 30 kb. In one embodiment, the insert nucleic acid is from about 30 kb to about 40 kb. In one embodiment, the insert nucleic acid is from about 40 kb to about 50 kb. In one embodiment, the insert nucleic acid is from about 60 kb to about 70 kb. In one embodiment, the insert nucleic acid is from about 80 kb to about 90 kb. In one embodiment, the insert nucleic acid is from about 90 kb to about 100 kb. In one embodiment, the insert nucleic acid is from about 100 kb to about 110 kb. In one embodiment, the insert nucleic acid is from about 120 kb to about 130 kb. In one embodiment, the insert nucleic acid is from about 130 kb to about 140 kb. In one embodiment, the insert nucleic acid is from about 140 kb to about 150 kb. In one embodiment, the insert nucleic acid is from about 150 kb to about 160 kb. In one embodiment, the insert nucleic acid is from about 160 kb to about 170 kb. In one embodiment, the insert nucleic acid is from about 170 kb to about 180 kb. In one embodiment, the insert nucleic acid is from about 180 kb to about 190 kb. In one embodiment, the insert nucleic acid is from about 190 kb to about 200 kb.

In one embodiment, the insert nucleic acid comprises a nucleic acid flanked with site-specific recombination target sequences. In one embodiment, the nucleic acid comprises a genomic nucleic acid. In one embodiment, the genomic nucleic acid is derived from a mouse, a human, or a combination thereof. In one embodiment, the site-specific recombination target sequences are selected from the group consisting of loxP, lox511, lox2272, lox66, lox71, loxM2, lox5171, FRT, FRT11, FRT71, attp, att, FRT, rox, and a combination thereof.

In one embodiment, the insert nucleic acid comprises a conditional allele. In one embodiment, the conditional allele is a multifunctional allele, as described in US 2011/0104799, which is incorporated by reference in its entirety. In one embodiment, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

In one embodiment, the insert nucleic acid comprises a selection cassette. In one embodiment, the selection cassette comprises a nucleic acid sequence encoding a selection marker, wherein the nucleic acid sequence is operably linked to a promoter. In one embodiment, the promoter is active in a prokaryotic cell. In one embodiment, the nucleic acid is active in both prokaryotic and eukaryotic cells. In one embodiment, the selection cassette is flanked with site-specific recombination target sequences. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof.

In one embodiment, the insert nucleic acid comprises a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. In one embodiment, the reporter gene is expressed under a control of an inducible promoter. In one embodiment, the reporter gene is expressed under a control of an endogenous promoter. In one embodiment, the reporter gene is expressed under a control of an exogenous promoter. In one embodiment, the reporter gene is expressed in a specific cell type. In one embodiment, the reporter gene is expressed in a tissue-specific manner. In one embodiment, the reporter gene is expressed in a developmental stage-specific manner.

In one embodiment, integration of the insert nucleic acid into the target genomic locus introduces one or more genetic modifications as described herein. In one embodiment, the genetic modification is a deletion of an endogenous nucleic acid sequence. In one embodiment, the genetic modification is an addition of an exogenous nucleic acid sequence into the target genomic locus. In one embodiment, the genetic modification is a replacement of an endogenous nucleic acid sequence with an exogenous nucleic acid sequence at the target genomic locus. In one embodiment, the exogenous nucleic acid sequence is a non-mouse nucleic acid sequence. In one embodiment, the exogenous nucleic acid sequence is a human nucleic acid sequence. In one embodiment, the genetic modification is a knockout, a deletion, an insertion, a replacement ("knock-in"), a point mutation, a domain swap, an exon swap, an intron swap, a regulatory sequence swap, a gene swap, or a combination thereof.

In one embodiment, the insert nucleic acid is homologous to a mouse nucleic acid sequence. In one embodiment, the insert nucleic acid is a human nucleic acid. In one embodiment, the insert nucleic acid is a fragment of a genomic nucleic acid. In one embodiment, the genomic nucleic acid is a mouse genomic nucleic acid, a human genomic nucleic acid, or a combination thereof. In one embodiment, the insert nucleic acid ranges from about 5 kb to about 200 kb as described above.

In one embodiment, the insert nucleic acid is orthologous to a mouse nucleic acid sequence. In one embodiment, the insert nucleic acid is a human nucleic acid. In one embodiment, the insert nucleic acid is a fragment of a genomic nucleic acid. In one embodiment, the genomic nucleic acid is a mouse genomic nucleic acid, a human genomic nucleic acid, or a combination thereof. In one embodiment, the insert nucleic acid ranges from about 5 kb to about 200 kb as described above.

In one embodiment, the insert nucleic acid comprises a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the insert nucleic acid comprises a genomic locus that encodes a protein expressed in a bone marrow or a bone marrow-derived cell. In one embodiment, the insert nucleic acid comprises a genomic locus that encodes a protein expressed in a spleen cell. In one embodiment, the genomic locus comprises a mouse genomic nucleic acid sequence, a human genomic nucleic acid sequence, or a combination thereof. In one embodiment, the nucleic acid comprises a genomic locus that encodes a protein expressed in a B cell. In one embodiment, the nucleic acid comprises a genomic locus that encodes a protein expressed in an immature B cell. In one embodiment, the nucleic acid comprises a genomic locus that encodes a protein expressed in a mature B cell.

In one embodiment, the insert nucleic acid comprises a genomic nucleic acid sequence that encodes a human immunoglobulin heavy chain variable region amino acid sequence. In one embodiment, the genomic nucleic acid sequence comprises an unrearranged human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a mouse immunoglobulin heavy chain constant region nucleic acid sequence or human immunoglobulin heavy chain constant region nucleic acid sequence, or a combination thereof. In one embodiment, the immunoglobulin heavy chain constant region nucleic acid sequence is selected from a $C_H1$, a hinge, a $C_H2$, a $C_H3$, and a combination thereof. In one embodiment, the heavy chain constant region nucleic acid sequence comprises a $C_H1$-hinge-$C_H2$-$C_H3$. In one embodiment, the genomic nucleic acid sequence comprises a rearranged human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a mouse immunoglobulin heavy chain constant region nucleic acid sequence or a human immunoglobulin heavy chain constant region nucleic acid sequence, or a combination thereof. In one embodiment, the immunoglobulin heavy chain constant region nucleic acid sequence is selected from a $C_H1$, a hinge, a $C_H2$, a $C_H3$, and a combination thereof. In one embodiment, the heavy chain constant region nucleic acid sequence comprises a $C_H1$-hinge-$C_H2$-$C_H3$.

In one embodiment, the insert nucleic acid comprises a genomic nucleic acid sequence that encodes a human immunoglobulin light chain variable region amino acid sequence. In one embodiment, the genomic nucleic acid sequence comprises an unrearranged human λ and/or κ light chain variable region nucleic acid sequence. In one embodiment, the genomic nucleic acid sequence comprises a rearranged human λ and/or κ light chain variable region nucleic acid sequence. In one embodiment, the unrearranged or rearranged λ and/or κ light chain variable region nucleic acid sequence is operably linked to a mouse, rat, or human immunoglobulin light chain constant region nucleic acid sequence selected from a λ light chain constant region nucleic acid sequence and a κ light chain constant region nucleic acid sequence.

In one embodiment, the insert nucleic acid comprises a human nucleic acid sequence. In one embodiment, the human nucleic acid sequence encodes an extracellular protein. In one embodiment, the human nucleic acid sequence encodes a ligand for a receptor. In one embodiment, the ligand is a cytokine. In one embodiment, the cytokine is a chemokine selected from CCL, CXCL, CX3CL, and XCL. In one embodiment, the cytokine is a tumor necrosis factor (TNF). In one embodiment, the cytokine is an interleukin (IL). In one embodiment, the interleukin is selected from IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36. In one embodiment, the interleukin is IL-2. In one embodiment, the human genomic nucleic acid sequence encodes a cytoplasmic protein. In one embodiment, the human genomic nucleic acid sequence encodes a membrane protein. In one embodiment, the membrane protein is a receptor. In one embodiment, the receptor is a cytokine receptor. In one embodiment, the cytokine receptor is an interleukin receptor. In one embodiment, the interleukin receptor is an interleukin 2 receptor alpha. In one embodiment, the interleukin receptor is an interleukin 2 receptor beta. In one embodiment, the interleukin receptor is an interleukin 2 receptor gamma. In one embodiment, the human genomic nucleic acid sequence encodes a nuclear protein. In one embodiment, the nuclear protein is a nuclear receptor.

In one embodiment, the insert nucleic acid comprises a genetic modification in a coding sequence. In one embodiment, the genetic modification comprises a deletion mutation of a coding sequence. In one embodiment, the genetic modification comprises a fusion of two endogenous coding sequences.

In one embodiment, the insert nucleic acid comprises a human nucleic acid sequence encoding a mutant human protein. In one embodiment, the mutant human protein is characterized by an altered binding characteristic, altered localization, altered expression, and/or altered expression pattern. In one embodiment, the human nucleic acid sequence comprises at least one human disease allele. In one embodiment, the human disease allele is an allele of a neurological disease. In one embodiment, the human disease allele is an allele of a cardiovascular disease. In one embodiment, the human disease allele is an allele of a kidney disease. In one embodiment, the human disease allele is an allele of a muscle disease. In one embodiment, the human disease allele is an allele of a blood disease. In one embodiment, the human disease allele is an allele of a cancer-causing gene. In one embodiment, the human disease allele is an allele of an immune system disease. In one embodiment, the human disease allele is a dominant allele. In one embodiment, the human disease allele is a recessive allele. In one embodiment, the human disease allele comprises a single nucleotide polymorphism (SNP) allele.

In one embodiment, the insert nucleic acid comprises a regulatory sequence. In one embodiment, the regulatory sequence is a promoter sequence. In one embodiment, the regulatory sequence is an enhancer sequence. In one embodiment, the regulatory sequence is a transcriptional repressor-binding sequence. In one embodiment, the insert nucleic acid comprises a human nucleic acid sequence, wherein the human nucleic acid sequence comprises a deletion of a non-protein-coding sequence, but does not comprise a deletion of a protein-coding sequence. In one embodiment, the deletion of the non-protein-coding sequence comprises a deletion of a regulatory sequence. In one embodiment, the deletion of the regulatory element comprises a deletion of a promoter sequence. In one embodiment, the deletion of the regulatory element comprises a deletion of an enhancer sequence.

In one aspect, a method for modifying a target genomic locus in a mammalian cell is provided, comprising introducing into a mammalian cell: (i) a nuclease agent that makes a singe or double-strand break at or near the target genomic locus, and (ii) a large targeting vector (LTVEC) comprising an insert nucleic acid flanked with an upstream homology arm and a downstream homology arm.

In one embodiment, the mammalian cell is a pluripotent cell. In one embodiment, the pluripotent cell is an embryonic stem (ES) cell. In one embodiment, the pluripotent cell is a non-human ES cell. In one embodiment, the pluripotent cell is an induced pluripotent stem (iPS) cell. In one embodiment, the induced pluripotent (iPS) cell is derived from a fibroblast. In one embodiment, the induced pluripotent (iPS) cell is derived from a human fibroblast. In one embodiment, the pluripotent cell is a hematopoietic stem cell (HSC). In one embodiment, the pluripotent cell is a neuronal stem cell (NSC). In one embodiment, the pluripotent cell is an epiblast stem cell. In one embodiment, the pluripotent cell is a developmentally restricted progenitor cell.

In one embodiment, the pluripotent cell is a rodent pluripotent cell. In one embodiment, the rodent pluripotent cell is a rat pluripotent cell. In one embodiment, the rat pluripotent cell is a rat ES cell. In one embodiment, the rodent pluripotent cell is a mouse pluripotent cell. In one embodiment, the pluripotent cell is a mouse embryonic stem (ES) cell.

In one embodiment, the mammalian cell is an immortalized mouse or rat cell. In one embodiment, the mammalian cell is an immortalized human cell. In one embodiment, the mammalian cell is a human fibroblast. In one embodiment, the mammalian cell is a cancer cell. In one embodiment, the mammalian cell is a human cancer cell.

In one embodiment, the mammalian cell is a human cell isolated from a patient having a disease. In one embodiment, the human cell comprises a human nucleic acid sequence encoding a mutant protein. In one embodiment, the mutant human protein is characterized by an altered binding characteristic, altered localization, altered expression, and/or altered expression pattern. In one embodiment, the human nucleic acid sequence comprises at least one human disease allele. In one embodiment, the human nucleic acid sequence comprises at least one human disease allele. In one embodiment, the human disease allele is an allele of a neurological disease. In one embodiment, the human disease allele is an allele of a cardiovascular disease. In one embodiment, the human disease allele is an allele of a kidney disease. In one embodiment, the human disease allele is an allele of a muscle disease. In one embodiment, the human disease allele is an allele of a blood disease. In one embodiment, the human disease allele is an allele of a cancer-causing gene. In one embodiment, the human disease allele is an allele of an immune system disease. In one embodiment, the human disease allele is a dominant allele. In one embodiment, the human disease allele is a recessive allele. In one embodiment, the human disease allele comprises a single nucleotide polymorphism (SNP) allele.

In one embodiment, the target genomic locus is selected from an FcER1a locus, a TLR4 locus, a PRLR locus, a Notch4 locus, an Accn2 locus, an Adamts5 locus, a TRPA1 locus, FolH1 locus, an LRP5 locus, and an ERBB4 locus.

In one embodiment, the target genomic locus comprises a human genomic sequence. In one embodiment, the target genomic locus comprises a genomic nucleic acid sequence of non-human animal. In one embodiment, the non-human animal is a rodent. In one embodiment, the rodent is selected from a mouse, a rat, and a hamster.

In one embodiment, the at least one human disease allele described above that is located at the target genomic locus is replaced with the insert nucleic acid. In one embodiment, the replacement of the human disease allele is mediated by a knockout, a deletion, an insertion, a replacement ("knock-in"), a domain swap, an exon swap, an intron swap, a regulatory sequence swap, a gene swap, or a combination thereof.

In one embodiment, the nuclease agent is introduced together with the large targeting vector (LTVEC). In one embodiment, the nuclease agent is introduced separately from the LTVEC over a period of time. In one embodiment, the nuclease agent is introduced prior to the introduction of the LTVEC. In one embodiment, the nuclease agent is introduced following introduction of the LTVEC.

In one embodiment, combined use of the LTVEC with the nuclease agent results in an increased targeting efficiency compared to use of the LTVEC alone. In one embodiment, when the LTVEC is used in conjunction with the nuclease agent, targeting efficiency of the LTVEC is increased at least by two-fold compared to when the LTVEC is used alone. In one embodiment, when the LTVEC is used in conjunction with the nuclease agent, targeting efficiency of the LTVEC is increased at least by three-fold compared to when the LTVEC is used alone. In one embodiment, when the LTVEC is used in conjunction with the nuclease agent, targeting efficiency of the LTVEC is increased at least by four-fold compared to when the LTVEC is used alone.

In one embodiment, the nuclease agent is an expression construct comprising a nucleic acid sequence encoding a nuclease, wherein the nucleic acid sequence is operably linked to a promoter. In one embodiment, the promoter is a constitutively-active promoter. In one embodiment, the promoter is an inducible promoter. In one embodiment, the promoter is active in the mammalian cell. In one embodiment, the nuclease agent is an mRNA encoding an endonuclease.

In one embodiment, the nuclease agent is a zinc-finger nuclease (ZFN). In one embodiment, each monomer of the ZFN comprises 3 or more zinc finger-based DNA binding domains, wherein each zinc finger-based DNA binding domain binds to a 3 bp subsite. In one embodiment, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site, and wherein the FokI nucleases dimerize and make a double strand break.

In one embodiment, the nuclease agent is a Transcription Activator-Like Effector Nuclease (TALEN). In one embodiment, each monomer of the TALEN comprises 12-25 TAL repeats, wherein each TAL repeat binds a 1 bp subsite. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by about 6 bp to about 40 bp cleavage site, and wherein the FokI nucleases dimerize and make a double strand break.

In one embodiment, each monomer of the nuclease recognizes a target sequence of at least 9 nucleotides. In one embodiment, the target sequence is from about 9 to about 12 nucleotides in length. In one embodiment, the target sequence is from about 12 to about 15 nucleotides in length. In one embodiment, the target sequence is from about 15 to about 18 nucleotides in length. In one embodiment, the target sequence is from about 18 to about 21 nucleotides in length.

In one embodiment, a target nucleic acid sequence of the nuclease agent is located in an intron. In one embodiment, the target nucleic acid sequence is located in an exon. In one embodiment, the target nucleic acid sequence is located in a promoter. In one embodiment, the target nucleic acid sequence is in a non-protein-coding region. In one embodiment, the non-protein-coding region is a regulatory region. In one embodiment, the target nucleic acid sequence is located in a promoter regulatory region. In one embodiment, the target nucleic acid sequence is located in an enhancer region.

In one embodiment, the nuclease agent is a meganuclease. In one embodiment, the meganuclease recognizes double-stranded DNA sequences of 12 to 40 base pairs. In one embodiment, the meganuclease recognize one perfectly matched target sequence in the genome. In one embodiment, the meganuclease is a homing nuclease. In one embodiment, the homing nuclease is a LAGLIDADG family of homing nuclease. In one embodiment, the LAGLIDADG family of homing nuclease is selected from I-SceI, I-CreI, and I-DmoI.

In one embodiment, the LTVEC ranges from about 50 kb to about 300 kb. In one embodiment, the LTVEC ranges from about 50 kb to about 75 kb. In one embodiment, the LTVEC ranges from about 75 kb to about 100 kb. In one embodiment, the LTVEC ranges from about 100 kb to 125 kb. In one embodiment, the LTVEC ranges from about 125 kb to about 150 kb. In one embodiment, the LTVEC ranges from about 150 kb to about 175 kb. In one embodiment, the LTVEC ranges from about 175 kb to about 200 kb. In one embodiment, the LTVEC ranges from about 200 kb to about 225 kb. In one embodiment, the LTVEC ranges from about 225 kb to about 250 kb. In one embodiment, the LTVEC ranges from about 250 kb to about 275 kb. In one embodiment, the LTVEC ranges from about 275 kb to about 300 kb.

In one embodiment, the homology arms of the LTVEC are derived from a BAC library, a cosmid library, or a P1 phage library. In one embodiment, the homology arms are derived from a genomic locus of the non-human animal that is not targetable using a conventional method. In one embodiment, the homology arms are derived from a synthetic DNA.

In one embodiment, a sum total of the upstream homology arm and the downstream homology arm is at least 10 kb. In one embodiment, the upstream homology arm ranges from about 5 kb to about 100 kb. In one embodiment, the downstream homology arm ranges from about 5 kb to about 100 kb. In one embodiment, the upstream and the downstream homology arms range from about 5 kb to about 10 kb. In one embodiment, the upstream and the downstream homology arms range from about 10 kb to about 20 kb. In one embodiment, the upstream and the downstream homology arms range from about 20 kb to about 30 kb. In one embodiment, the upstream and the downstream homology arms range from about 30 kb to about 40 kb. In one embodiment, the upstream and the downstream homology arms range from about 40 kb to about 50 kb. In one embodiment, the upstream and the downstream homology arms range from about 50 kb to about 60 kb. In one embodiment, the upstream and the downstream homology arms range from about 60 kb to about 70 kb. In one embodiment, the upstream and the downstream homology arms range from about 70 kb to about 80 kb. In one embodiment, the upstream and the downstream homology arms range from about 80 kb to about 90 kb. In one embodiment, the upstream and the downstream homology arms range from about 90 kb to about 100 kb. In one embodiment, the upstream and the downstream homology arms range from about 100 kb to about 110 kb. In one embodiment, the upstream and the downstream homology arms range from about 110 kb to about 120 kb. In one embodiment, the upstream and the downstream homology arms range from about 120 kb to about 130 kb. In one embodiment, the upstream and the downstream homology arms range from about 130 kb to about 140 kb. In one embodiment, the upstream and the downstream homology arms range from about 140 kb to about 150 kb. In one embodiment, the upstream and the downstream homology arms range from about 150 kb to about 160 kb. In one embodiment, the upstream and the downstream homology arms range from about 160 kb to about 170 kb. In one embodiment, the upstream and the downstream homology arms range from about 170 kb to about 180 kb. In one embodiment, the upstream and the downstream homology arms range from about 180 kb to about 190 kb. In one embodiment, the upstream and the downstream homology arms range from about 190 kb to about 200 kb.

In one embodiment, the targeting vector comprises a selection cassette. In one embodiment, the selection cassette comprises a nucleic acid sequence encoding a selection marker, wherein the nucleic acid sequence is operably linked to a promoter. In one embodiment, the promoter is active in a mammalian cell. In one embodiment, the promoter is active both in prokaryotic and eukaryotic cells. In one embodiment, the selection marker is selected from neomycin phosphotransferase (nea$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof.

In one embodiment, the insert nucleic acid is from about 5 kb to about 200 kb. In one embodiment, the insert nucleic acid is from about 5 kb to about 10 kb. In one embodiment, the insert nucleic acid is from about 10 kb to about 20 kb. In one embodiment, the insert nucleic acid is from about 20 kb to about 30 kb. In one embodiment, the insert nucleic acid is from about 30 kb to about 40 kb. In one embodiment, the insert nucleic acid is from about 40 kb to about 50 kb. In one embodiment, the insert nucleic acid is from about 60 kb to about 70 kb. In one embodiment, the insert nucleic acid is from about 80 kb to about 90 kb. In one embodiment, the insert nucleic acid is from about 90 kb to about 100 kb. In one embodiment, the insert nucleic acid is from about 100 kb to about 110 kb. In one embodiment, the insert nucleic acid is from about 120 kb to about 130 kb. In one embodiment, the insert nucleic acid is from about 130 kb to about 140 kb. In one embodiment, the insert nucleic acid is from about 140 kb to about 150 kb. In one embodiment, the insert nucleic acid is from about 150 kb to about 160 kb. In one embodiment, the insert nucleic acid is from about 160 kb to about 170 kb. In one embodiment, the insert nucleic acid is from about 170 kb to about 180 kb. In one embodiment, the insert nucleic acid is from about 180 kb to about 190 kb. In one embodiment, the insert nucleic acid is from about 190 kb to about 200 kb.

In one embodiment, the insert nucleic acid comprises a nucleic acid flanked with site-specific recombination target sequences. In one embodiment, the nucleic acid comprises a genomic nucleic acid. In one embodiment, the genomic nucleic acid is derived from a mouse, a human, or a combination thereof. In one embodiment, the site-specific recombination target sequences are selected from the group consisting of loxP, lox511, lox2272, lox66, lox71, loxM2, lox5171, FRT, FRT11, FRT71, attp, att, FRT, rox, and a combination thereof.

In one embodiment, the insert nucleic acid comprises a conditional allele. In one embodiment, the conditional allele is a multifunctional allele, as described in US 2011/0104799, which is incorporated by reference in its entirety. In one embodiment, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

In one embodiment, the insert nucleic acid comprises a selection cassette. In one embodiment, the selection cassette comprises a nucleic acid sequence encoding a selection marker, wherein the nucleic acid sequence is operably linked to a promoter. In one embodiment, the promoter is active in a mammalian cell. In one embodiment, the nucleic acid is active in a eukaryotic cell. In one embodiment, the selection cassette is flanked with site-specific recombination target sequences. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof.

In one embodiment, the insert nucleic acid comprises a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. In one embodiment, the reporter gene is expressed under a control of an inducible promoter. In one embodiment, the reporter gene is expressed under a control of an endogenous promoter. In one embodiment, the reporter gene is expressed under a control of an exogenous promoter. In one embodiment, the reporter gene is expressed in a specific cell type. In one embodiment, the reporter gene is expressed in a tissue-specific manner. In one embodiment, the reporter gene is expressed in a developmental stage-specific manner.

In one embodiment, integration of the insert nucleic acid into the target genomic locus introduces one or more genetic modifications as described herein. In one embodiment, the genetic modification is a deletion of an endogenous nucleic acid sequence. In one embodiment, the genetic modification is an addition of an exogenous nucleic acid sequence into the target genomic locus. In one embodiment, the genetic modification is a replacement of an endogenous nucleic acid sequence with an exogenous nucleic acid sequence at the target genomic locus. In one embodiment, the exogenous nucleic acid sequence is a non-mouse nucleic acid sequence. In one embodiment, the exogenous nucleic acid sequence is a human nucleic acid sequence. In one embodiment, the genetic modification is a knockout, a deletion, an insertion, a replacement ("knock-in"), a point mutation, a domain swap, an exon swap, an intron swap, a regulatory sequence swap, a gene swap, or a combination thereof.

In one embodiment, the insert nucleic acid is homologous to a mouse nucleic acid sequence. In one embodiment, the insert nucleic acid is a human nucleic acid. In one embodiment, the insert nucleic acid is a fragment of a genomic nucleic acid. In one embodiment, the genomic nucleic acid is a mouse genomic nucleic acid, a human genomic nucleic acid, or a combination thereof. In one embodiment, the insert nucleic acid ranges from about 5 kb to about 200 kb as described above.

In one embodiment, the insert nucleic acid is orthologous to a mouse nucleic acid sequence. In one embodiment, the insert nucleic acid is a human nucleic acid. In one embodiment, the insert nucleic acid is a fragment of a genomic nucleic acid. In one embodiment, the genomic nucleic acid is a mouse genomic nucleic acid, a human genomic nucleic acid, or a combination thereof. In one embodiment, the insert nucleic acid ranges from about 5 kb to about 200 kb as described above.

In one embodiment, the insert nucleic acid comprises a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the insert nucleic acid comprises a genomic locus that encodes a protein expressed in a bone marrow or a bone marrow-derived cell. In one embodiment, the insert nucleic acid comprises a genomic locus that encodes a protein expressed in a spleen cell. In one embodiment, the genomic locus comprises a mouse genomic nucleic acid sequence, a human genomic nucleic acid sequence, or a combination thereof. In one embodiment, the nucleic acid comprises a genomic locus that encodes a protein expressed in a B cell. In one embodiment, the nucleic acid comprises a genomic locus that encodes a protein expressed in an immature B cell. In one embodiment, the nucleic acid comprises a genomic locus that encodes a protein expressed in a mature B cell.

In one embodiment, the insert nucleic acid comprises a genomic nucleic acid sequence that encodes a human immunoglobulin heavy chain variable region amino acid sequence.

In one embodiment, the genomic nucleic acid sequence comprises an unrearranged human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a mouse immunoglobulin heavy chain constant region nucleic acid sequence or human immunoglobulin heavy chain constant region nucleic acid sequence, or a combination thereof. In one embodiment, the immunoglobulin heavy chain constant region nucleic acid sequence is selected from a $C_H1$, a hinge, a $C_H2$, a $C_H3$, and a combination thereof. In one embodiment, the heavy chain constant region nucleic acid sequence comprises a $C_H1$-hinge-$C_H2$-$C_H3$. In one embodiment, the genomic nucleic acid sequence comprises a rearranged human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a mouse immunoglobulin heavy chain constant region nucleic acid sequence or a human immunoglobulin heavy chain constant region nucleic acid sequence, or a combination thereof. In one embodiment, the immunoglobulin heavy chain constant region nucleic acid sequence is selected from a $C_H1$, a hinge, a $C_H2$, a $C_H3$, and a combination thereof. In one embodiment, the heavy chain constant region nucleic acid sequence comprises a $C_H1$-hinge-$C_H2$-$C_H3$.

In one embodiment, the insert nucleic acid comprises a genomic nucleic acid sequence that encodes a human immunoglobulin light chain variable region amino acid sequence. In one embodiment, the genomic nucleic acid sequence comprises an unrearranged human λ and/or κ light chain variable region nucleic acid sequence. In one embodiment, the genomic nucleic acid sequence comprises a rearranged human λ and/or κ light chain variable region nucleic acid sequence. In one embodiment, the unrearranged or rearranged λ and/or κ light chain variable region nucleic acid sequence is operably linked to a mouse or human immunoglobulin light chain constant region nucleic acid sequence selected from a λ light chain constant region nucleic acid sequence and a κ light chain constant region nucleic acid sequence.

In one embodiment, the insert nucleic acid comprises a human nucleic acid sequence. In one embodiment, the human nucleic acid sequence encodes an extracellular protein. In one embodiment, the human nucleic acid sequence encodes a ligand for a receptor. In one embodiment, the ligand is a cytokine. In one embodiment, the cytokine is a chemokine selected from CCL, CXCL, CX3CL, and XCL. In one embodiment, the cytokine is a tumor necrosis factor (TNF). In one embodiment, the cytokine is an interleukin (IL). In one embodiment, the interleukin is selected from IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36. In one embodiment, the interleukin is IL-2. In one embodiment, the human genomic nucleic acid sequence encodes a cytoplasmic protein. In one embodiment, the human genomic nucleic acid sequence encodes a membrane protein. In one embodiment, the membrane protein is a receptor. In one embodiment, the receptor is a cytokine receptor. In one embodiment, the cytokine receptor is an interleukin receptor. In one embodiment, the interleukin receptor is an interleukin 2 receptor alpha. In one embodiment, the interleukin receptor is an interleukin 2 receptor beta. In one embodiment, the interleukin receptor is an interleukin 2 receptor gamma. In one embodiment, the human genomic nucleic acid sequence encodes a nuclear protein. In one embodiment, the nuclear protein is a nuclear receptor.

In one embodiment, the insert nucleic acid comprises a genetic modification in a coding sequence. In one embodiment, the genetic modification comprises a deletion mutation of a coding sequence. In one embodiment, the genetic modification comprises a fusion of two endogenous coding sequences.

In one embodiment, the insert nucleic acid comprises a human nucleic acid sequence encoding a mutant human protein. In one embodiment, the mutant human protein is characterized by an altered binding characteristic, altered localization, altered expression, and/or altered expression pattern. In one embodiment, the human nucleic acid sequence comprises at least one human disease allele. In one embodiment, the human disease allele is an allele of a neurological disease. In one embodiment, the human disease allele is an allele of a cardiovascular disease. In one embodiment, the human disease allele is an allele of a kidney disease. In one embodiment, the human disease allele is an allele of a muscle disease. In one embodiment, the human disease allele is an allele of a blood disease. In one embodiment, the human disease allele is an allele of a cancer-causing gene. In one embodiment, the human disease allele is an allele of an immune system disease. In one embodiment, the human disease allele is a dominant allele. In one embodiment, the human disease allele is a recessive allele. In one embodiment, the human disease allele comprises a single nucleotide polymorphism (SNP) allele.

In one embodiment, the insert nucleic acid comprises a regulatory sequence. In one embodiment, the regulatory sequence is a promoter sequence. In one embodiment, the regulatory sequence is an enhancer sequence. In one embodiment, the regulatory sequence is a transcriptional repressor-binding sequence. In one embodiment, the insert nucleic acid comprises a human nucleic acid sequence, wherein the human nucleic acid sequence comprises a deletion of a non-protein-coding sequence, but does not comprise a deletion of a protein-coding sequence. In one embodiment, the deletion of the non-protein-coding sequence comprises a deletion of a regulatory sequence. In one embodiment, the deletion of the regulatory element comprises a deletion of a promoter sequence. In one embodiment, the deletion of the regulatory element comprises a deletion of an enhancer sequence.

In one aspect, a mammalian cell made with a method as described herein is provided. In one embodiment, the mammalian cell comprises an insert nucleic acid comprising one or more genetic modifications as described herein at a target genomic locus.

In one embodiment, the mammalian cell is a pluripotent cell. In one embodiment, the pluripotent cell is an embryonic stem (ES) cell. In one embodiment, the pluripotent cell is an induced pluripotent stem (iPS) cell. In one embodiment, the induced pluripotent (iPS) cell is derived from a fibroblast. In one embodiment, the induced pluripotent (iPS) cell is derived from a human fibroblast. In one embodiment, the pluripotent cell is a hematopoietic stem cell (HSC). In one embodiment, the pluripotent cell is a neuronal stem cell (NSC). In one embodiment, the pluripotent cell is an epiblast stem cell. In one embodiment, the pluripotent cell is a developmentally restricted progenitor cell.

In one embodiment, the pluripotent cell is a mouse pluripotent cell. In one embodiment, the pluripotent cell is a mouse embryonic stem (ES) cell.

In one embodiment, the mammalian cell is an immortalized mouse or rat cell. In one embodiment, the mammalian cell is an immortalized human cell. In one embodiment, the mammalian cell is a human fibroblast. In one embodiment, the mammalian cell is a cancer cell. In one embodiment, the mammalian cell is a human cancer cell.

In one embodiment, the target genomic locus is selected from an FcER1a locus, a TLR4 locus, a PRLR locus, a Notch4 locus, an Accn2 locus, an Adamts5 locus, a TRPA1 locus, FolH1 locus, an LRP5 locus, and an ERBB4 locus.

In one embodiment, the target genomic locus comprises one or more genetic modifications as described herein. In one embodiment, the genetic modification is a deletion of an endogenous nucleic acid sequence. In one embodiment, the genetic modification is an addition of an exogenous nucleic acid sequence into the target genomic locus. In one embodiment, the genetic modification is a replacement of an endogenous nucleic acid sequence with an exogenous nucleic acid sequence at the target genomic locus. In one embodiment, the exogenous nucleic acid sequence is a non-mouse nucleic acid sequence. In one embodiment, the exogenous nucleic acid sequence is a human nucleic acid sequence. In one embodiment, the target genomic locus comprises a modification selected from a knockout, a deletion, an insertion, a replacement ("knock-in"), a domain swap, an exon swap, an intron swap, a regulatory sequence swap, a gene swap, and a combination thereof.

In one embodiment, the target genomic locus comprises an insert nucleic acid that is homologous to a mouse nucleic acid sequence. In one embodiment, the insert nucleic acid is a human nucleic acid. In one embodiment, the insert nucleic acid is a fragment of a genomic nucleic acid. In one embodiment, the genomic nucleic acid is a mouse genomic nucleic acid, a human genomic nucleic acid, or a combination thereof. In one embodiment, the insert nucleic acid ranges from about 5 kb to about 200 kb as described above.

In one embodiment, the target genomic locus comprises an insert nucleic acid that is orthologous to a mouse nucleic acid sequence. In one embodiment, the insert nucleic acid is a human nucleic acid. In one embodiment, the insert nucleic acid is a fragment of a genomic nucleic acid. In one embodiment, the genomic nucleic acid is a mouse genomic nucleic acid, a human genomic nucleic acid, or a combination thereof. In one embodiment, the insert nucleic acid ranges from about 5 kb to about 200 kb as described above.

In one embodiment, the target genomic locus comprises a conditional allele. In one embodiment, the conditional allele is a multifunctional allele, as described in US 2011/0104799, which is incorporated by reference in its entirety. In one embodiment, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

In one embodiment, the insert nucleic acid comprises a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. In one embodiment, the reporter gene is expressed under a control of an inducible promoter. In one embodiment, the reporter gene is expressed under a control of an endogenous promoter. In one embodiment, the reporter gene is expressed under a control of an exogenous promoter. In one embodiment, the reporter gene is expressed in a specific cell type. In one embodiment, the reporter gene is expressed in a tissue-specific manner. In one embodiment, the reporter gene is expressed in a developmental stage-specific manner.

In one embodiment, the insert nucleic acid comprises a human nucleic acid sequence encoding a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the human nucleic acid sequence encodes a protein expressed in a bone marrow or a bone marrow-derived cell. In one embodiment, the genome of the mouse ES cell comprises a human genomic locus that encodes a protein expressed in a spleen cell. In one embodiment, the human nucleic acid encodes a protein expressed in a B cell. In one embodiment, the human nucleic acid encodes a protein expressed in an immature B cell. In one embodiment, the human nucleic acid encodes a protein expressed in a mature B cell.

In one embodiment, the insert nucleic acid comprises a human nucleic acid sequence that encodes a human immunoglobulin heavy chain variable region amino acid sequence. In one embodiment, the human nucleic acid sequence comprises an unrearranged human immunoglobulin heavy chain variable region nucleic acid sequence. In one embodiment, the unrearranged human immunoglobulin heavy chain variable region nucleic acid sequence is operably linked to a mouse immunoglobulin heavy chain constant region nucleic acid sequence, a human immunoglobulin heavy chain constant region nucleic acid sequence, or a combination thereof. In one embodiment, the immunoglobulin heavy chain constant region nucleic acid sequence is selected from a $C_H1$, a hinge, a $C_H2$, a $C_H3$, and a combination thereof. In one embodiment, the heavy chain constant region nucleic acid sequence comprises a $C_H1$-hinge-$C_H2$-$C_H3$. In one embodiment, the human nucleic acid sequence comprises a rearranged human immunoglobulin heavy chain variable region nucleic acid sequence. In one embodiment, the human immunoglobulin heavy chain variable region nucleic acid sequence is operably linked to a mouse immunoglobulin heavy chain constant region nucleic acid sequence, a human immunoglobulin heavy chain constant region nucleic acid sequence, or a combination thereof. In one embodiment, the immunoglobulin heavy chain constant region nucleic acid sequence is selected from a $C_H1$, a hinge, a $C_H2$, a $C_H3$, and a combination thereof. In one embodiment, the heavy chain constant region nucleic acid sequence comprises a $C_H1$-hinge-$C_H2$-$C_H3$.

In one embodiment, the insert nucleic acid comprises a human nucleic acid sequence that encodes a human immunoglobulin light chain variable region amino acid sequence. In one embodiment, the human nucleic acid sequence comprises an unrearranged human λ and/or κ light chain variable region nucleic acid sequence. In one embodiment, the human nucleic acid sequence comprises a rearranged human λ and/or κ light chain variable region nucleic acid sequence. In one embodiment, the unrearranged λ and/or κ light chain variable region nucleic acid sequence is operably linked to a mouse or human immunoglobulin light chain constant region nucleic acid sequence selected from a λ light chain constant region nucleic acid sequence and a κ light chain constant region nucleic acid sequence.

In one embodiment, the insert nucleic acid comprises a human nucleic acid sequence. In one embodiment, the human nucleic acid sequence encodes an extracellular protein. In one embodiment, the human nucleic acid sequence encodes a ligand for a receptor. In one embodiment, the ligand is a cytokine. In one embodiment, the cytokine is a chemokine selected from CCL, CXCL, CX3CL, and XCL. In one embodiment, the cytokine is a tumor necrosis factor (TNF). In one embodiment, the cytokine is an interleukin (IL). In one embodiment, the interleukin is selected from IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36. In one embodiment, the interleukin is IL-2. In one embodiment, the human genomic nucleic acid sequence encodes a cytoplasmic protein. In one embodiment, the human genomic nucleic acid sequence encodes a membrane protein. In one embodiment, the membrane protein is a receptor. In one embodiment, the receptor is a cytokine receptor. In one embodiment, the cytokine receptor is an interleukin receptor. In one embodiment, the interleukin receptor is an interleukin 2 receptor alpha. In one embodiment, the interleukin receptor is an interleukin 2 receptor beta. In one embodiment, the interleukin receptor is an interleukin 2 receptor gamma. In one embodiment, the human genomic nucleic acid sequence encodes a nuclear protein. In one embodiment, the nuclear protein is a nuclear receptor.

In one embodiment, the insert nucleic acid comprises a genetic modification in a coding sequence. In one embodiment, the genetic modification comprises a deletion mutation of a coding sequence. In one embodiment, the genetic modification comprises a fusion of two endogenous coding sequences.

In one embodiment, the insert nucleic acid comprises a human nucleic acid sequence encoding a mutant human protein. In one embodiment, the mutant human protein is characterized by an altered binding characteristic, altered localization, altered expression, and/or altered expression pattern. In one embodiment, the human nucleic acid sequence comprises at least one human disease allele. In one embodiment, the human disease allele is an allele of a neurological disease. In one embodiment, the human disease allele is an allele of a cardiovascular disease. In one embodiment, the human disease allele is an allele of a kidney disease. In one embodiment, the human disease allele is an allele of a muscle disease. In one embodiment, the human disease allele is an allele of a blood disease. In one embodiment, the human disease allele is an allele of a cancer-causing gene. In one embodiment, the human disease allele is an allele of an immune system disease. In one embodiment, the human disease allele is a dominant allele. In one embodiment, the human disease allele is a recessive allele. In one embodiment, the human disease allele comprises a single nucleotide polymorphism (SNP) allele.

In one embodiment, the insert nucleic acid comprises a regulatory sequence. In one embodiment, the regulatory sequence is a promoter sequence. In one embodiment, the regulatory sequence is an enhancer sequence. In one embodiment, the regulatory sequence is a transcriptional repressor-binding sequence. In one embodiment, the insert nucleic acid comprises a human nucleic acid sequence, wherein the human nucleic acid sequence comprises a deletion of a non-protein-coding sequence, but does not comprise a deletion of a protein-coding sequence. In one embodiment, the deletion of the non-protein-coding sequence comprises a deletion of a regulatory sequence. In one embodiment, the deletion of the regulatory element comprises a deletion of a promoter sequence. In one embodiment, the deletion of the regulatory element comprises a deletion of an enhancer sequence.

In one aspect, a method for making a non-human animal comprising in its germline one or more genetic modifications as described herein is provided, comprising:

(a) modifying a genomic locus of interest of a non-human animal in a prokaryotic cell employing a large targeting vector (LTVEC) and a nuclease agent that generates a single or double-strand break at or near the genomic locus of interest, wherein the LTVEC comprises an insert nucleic acid flanked with upstream and downstream homology arms, and the prokaryotic cell is capable of expressing a recombinase;

(b) selecting a modified prokaryotic cell comprising a genetically modified LTVEC;

(c) isolating the genetically modified LTVEC;

(d) introducing the genetically modified LTVEC into a pluripotent cell of the non-human animal to generate a genetically modified pluripotent cell comprising the insert nucleic acid in the genomic locus of interest;

(e) selecting the genetically modified pluripotent cell;

(f) introducing the genetically modified pluripotent cell into a host embryo of the non-human animal at a pre-morula stage; and (g) implanting the host embryo comprising the genetically modified pluripotent cell into a surrogate mother to generate an F0 generation derived from the genetically modified pluripotent cell.

In one embodiment, the non-human animal is a mammal. In one embodiment, the mammal is a rodent. In one embodiment, the rodent is selected form a mouse, a rat, and a hamster. In one embodiment, the non-human animal is a mouse, and the pluripotent cell is a mouse ES cell. In one embodiment, the non-human animal is a rat, and the pluripotent cell is a rat ES cell.

In one embodiment, the target genomic locus comprises one or more genetic modifications as described herein.

In one embodiment, isolating step (c) further comprises (c)' linearizing the genetically modified LTVEC.

In one embodiment, introducing step (d) further comprises (d)' introducing a nuclease agent as described herein into the pluripotent cell. In one embodiment, the nuclease agent is a zinc finger nuclease (ZFN). In one embodiment, the nuclease agent is a Transcription Activator-Like Effector Nuclease (TALEN).

In one embodiment, selecting steps (b) and/or (e) are carried out by applying a selectable agent as described herein to the prokaryotic cell or the pluripotent cell.

In one embodiment, selecting steps (b) and/or (e) are carried out via a modification of allele (MOA) assay as described herein.

BRIEF DESCRIPTION OF THE DRAWINGS

FIG. 1 illustrates the Zinc Finger Nuclease (ZFN) cleavage site on the mouse Il2rg gene. The FIGURE was not scaled proportionally. The boxed sequences in the bottom panel represent ZFN target sequences.

DETAILED DESCRIPTION

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

Definitions

The term "embryonic stem cell" or "ES cell" as used herein includes an embryo-derived totipotent or pluripotent cell that is capable of undifferentiated proliferation in vitro, and is capable of contributing to any tissue of the developing embryo upon introduction into an embryo. The term "pluripotent cell" as used herein includes an undifferentiated cell that possesses the ability to develop into more than one differentiated cell type.

The term "germline" in reference to an immunoglobulin nucleic acid sequence includes a nucleic acid sequence that can be passed to progeny.

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four framework (FR) regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. Heavy chain variable domains are encoded by variable region nucleotide sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found in IMGT database, which is accessible via the internet on the world wide web (www) at the URL "imgt.org."

The phrase "light chain" includes an immunoglobulin light chain sequence from any organism, and unless otherwise specified includes human kappa (κ) and lambda (λ) light chains and a VpreB, as well as surrogate light chains. Light chain variable domains typically include three light chain CDRs and four FRs, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by the light chain variable region nucleotide sequence, which generally comprises light chain $V_L$ and light chain $J_L$ gene segments, derived from a repertoire of light chain V and J gene segments present in the germline. Sequences, locations and nomenclature for light chain V and J gene segments for various organisms can be found in IMGT database, which is accessible via the internet on the world wide web (www) at the URL "imgt.org." Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

The term "homologous nucleic acid" as used herein includes a nucleic acid sequence that is either identical or substantially similar to a known reference sequence. In one embodiment, the term "homologous nucleic acid" is used to characterize a DNA or RNA sequence having at least 70%, at least 75%, at least 80%, at least 85%, at least 90%, at least 95%, at least 96%, at least 97%, at least 98%, at least 99%, or even 100% identical to a known reference sequence.

The term "orthologous nucleic acid" as used herein includes a nucleic acid sequence from one species that is functionally equivalent to a known reference sequence in another species.

The term "large targeting vector" or "LTVEC" as used herein includes large targeting vectors for eukaryotic cells that are derived from fragments of cloned genomic nucleic acid larger than those typically used by other approaches intended to perform homologous targeting in eukaryotic cells. The size of the LTVEC is too large to enable screening of targeting events by conventional assays, e.g., southern blotting and long-range (e.g., 1 kb-5 kb) PCR. Examples of the LTVEC, include, but are not limited to, vectors derived from a bacterial artificial chromosome (BAC) and a yeast artificial chromosome (YAC).

The term "modification of allele" or "MOA" includes the modification of the exact DNA sequence of one allele of a gene(s) or chromosomal locus (loci) in a genome. Examples of "modification of allele (MOA)" include, but are not limited to, deletions, substitutions, or insertions of as little as a single nucleotide or deletions of many kilobases spanning a gene(s) or chromosomal locus (loci) of interest, as well as any and all possible modifications between these two extremes.

The term "nuclease" as used herein includes an agent that induces a break in a nucleic acid sequence, e.g., a single or a double strand break in a double-stranded DNA sequence. Nucleases include those which bind a preselected or specific sequence and cut at or near the preselected or specific sequence, e.g., engineered zinc finger nucleases and engineered TAL effector nucleases. Nucleases are not limited to ZFNs and TAL effector nuclease, but can be any nuclease suitable for use with an LTVEC to achieve improved targeting efficiency. Non-limiting examples include other zinc finger-based nucleases and engineered meganucleases that cut at preselected or specific sequences.

TAL effector nucleases suitable for use with the invention include any TAL nucleases known in the art. Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference). In various embodiments, TAL effector nucleases are engineered that cut in or near a target nucleic acid sequence in, e.g., a genome of interest, wherein the target nucleic acid sequence is at or near a sequence to be modified by an LTVEC. TAL effector nucleases are proteins that comprise an endonuclease domain and one or more TAL effector DNA binding domains, wherein the one or more TAL effector DNA binding domains comprise a sequence that recognizes a preselected or specific nucleic acid sequence. The TAL nucleases suitable for use with the invention include those that are specifically designed to bind at or near target nucleic acid sequences to be modified by LTVECs as described herein.

The phrase "operably linked" includes a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

The term "promoter" and "promoter regulatory element", and the like, as used herein include a nucleotide sequence element within a nucleic acid fragment or gene that controls the expression of that gene.

The term "recombination site" as used herein includes a nucleotide sequence that is recognized by a site-specific recombinase and that can serve as a substrate for a recombination event.

The term "site-specific recombinase" as used herein includes a group of enzymes that can facilitate recombination between "recombination sites" where the two recombination sites are physically separated within a single nucleic acid molecule or on separate nucleic acid molecules. Examples of "site-specific recombinase" include, but are not limited to, Cre, Flp, and Dre recombinases.

Modification of Genomic Loci Using an LTVEC and a Nuclease Agent

While progress has been made in targeting various genomic loci of non-human animals, there still remain many genomic loci or cell types that cannot be targeted with conventional targeting strategies. The reasons for the failure may vary, but, as used herein, include loci or cells that are either not targeted successfully at all, or are targeted improperly or at a significantly low efficiency by conventional targeting methods. Conventional targeting methods include targeting using homologous recombination employing conventional targeting vectors. Loci that are difficult to target include loci that cannot be targeted even with LTVECs alone, i.e., in the absence of assistance in the form of a recombinogenic single or double strand-break, or that are targeted with LTVECs improperly or at a low efficiency in the absence of the recombinogenic single or double-strand break.

Compositions and methods are provided for targeting nucleic acid sequences employing a nuclease agent capable of forming a recombinogenic single or double-strand break, in conjunction with a large targeting vector, or LTVEC, wherein the targeted nucleic acid sequence (or a sequence near the targeted nucleic acid sequence) is modified by the LTVEC. The compositions and methods are useful for modifying genomic nucleic acid sequences that are difficult or impossible to modify using conventional targeting strategies, even when using LTVECs alone.

In various aspects, compositions and methods are provided for employing an LTVEC to make a modification to a target nucleic acid, e.g., a locus in a genome, wherein the target nucleic acid comprises a target sequence that is to be modified by a sequence of the LTVEC (by homologous recombination of the target nucleic acid with the LTVEC), wherein a single or a double-strand break is made in the target nucleic acid at or near the target sequence.

The presence of a single or a double strand break at or near the target nucleic acid, in various embodiments, increases the efficiency and/or frequency of recombination between an LTVEC and a target nucleic acid. In one embodiment the recombination is homologous recombination. In another embodiment the recombination is an insertion by non-homologous end joining. In various embodiments, in the presence of the single or double strand bread, targeting efficiency of an LTVEC sequence at the target genomic locus is at least about 2-fold higher, at least about 3-fold higher, at least about 4-fold higher than in the absence of the single or double-strand break (using, e.g., the same LTVEC and the same target nucleic acid comprising the same target sequence but in the absence of an added nuclease that makes the single or double strand break).

LTVECs suitable for use with the invention, and methods for making them, are described, e.g., in U.S. Pat. Nos. 6,586,251, 6,596,541, 7,105,348, and WO 2002/036789 (PCT/US01/45375).

Although embodiments directed to introducing an LTVEC into a mouse pluripotent cell, e.g., a mouse ES cell, are extensively discussed, other methods that introduce an LTVEC into a variety of mammalian cell types are also provided herein. Such mammalian cells include any mammalian cells that can be genetically modified according to the method as disclosed herein, including, e.g., a mouse cell, a rat cell, a rabbit cell, a pig cell, a bovine cell, a deer cell, a sheep cell, a goat cell, a chicken cell, a cat cell, a dog cell, a ferret cell, a primate (e.g., marmoset, rhesus monkey) cell, and the like. In some embodiments, for those mammals for which suitable genetically modifiable pluripotent cells are not readily available, other methods are employed in order to reprogram somatic cells into pluripotent cells, e.g., via introduction into somatic cells of a combination of pluripotency-inducing factors, including, but not limited to, Oct3/4, Sox2, KLF4, Myc, Nanog, LIN28, and Glis1.

In one embodiment, the upstream and downstream homology arms are from the same genome as the targeted genome. In one embodiment, the homology arms are from a related genome, e.g., the targeted genome is a mouse genome of a first strain, and the targeting arms are from a mouse genome of a second strain, wherein the first strain and the second strain are different. In one embodiment, the targeting arms are derived from a BAC library, a cosmid library, or a P1 phage library. In one embodiment, the homology arms are derived from a synthetic DNA. In one embodiment, the homology arms are derived from a gene that is not targetable using conventional methods. In a specific embodiment, the homology arms are from a gene that cannot be targeted using conventional targeting technology, or can be targeted only incorrectly or only with significantly low efficiency, in the absence of a single or double-strand break induced by a nuclease agent.

In various embodiments, in order to facilitate identification of the targeted modification, a high-throughput quantitative assay, namely, modification of allele (MOA) assay, is employed. The MOA assay described herein allows a large-scale screening of a modified allele(s) in a parental chromosome following a genetic modification. The MOA assay can be carried out via various analytical techniques, including, but not limited to, a quantitative PCR, e.g., a real-time PCR (qPCR). For example, the real-time PCR comprises a first primer set that recognizes the target locus and a second primer set that recognizes a non-targeted reference locus. In addition, the primer set comprises a fluorescent probe that recognizes the amplified sequence. The quantitative assay can also be carried out via a variety of analytical techniques, including, but not limited to, fluorescence-mediated in situ hybridization (FISH), comparative genomic hybridization, isothermic DNA amplification, quantitative hybridization to an immobilized probe(s), Invader Probes®, MMP Assays®, TaqMan® Molecular Beacon, and Eclipse™ probe technology. (See, for example, US2005/0144655, incorporated by reference herein in its entirety).

In some embodiments, various genetic modifications of the target genomic loci described herein can be carried out by a series of homologous recombination reactions (BHR) in bacterial cells using an LTVEC derived from Bacterial Artificial Chromosome (BAC) DNA using VELOCI-GENE® genetic engineering technology (see, e.g., U.S. Pat. No. 6,586,251 and Valenzuela, D. M. et al. (2003), High-throughput engineering of the mouse genome coupled with high-resolution expression analysis, *Nature Biotechnology* 21(6): 652-659, which is incorporated herein by reference in their entireties).

In some embodiments, targeted mouse ES cells comprising various genetic modifications as described herein are used as donor ES cells and introduced into a pre-morula stage mouse embryo, e.g., an 8-cell stage mouse embryo, via the VELOCIMOUSE® method (see, e.g., U.S. Pat. Nos. 7,576,259, 7,659,442, 7,294,754, and US 2008-0078000 A1, all of which are incorporated by reference herein in their entireties). The mouse embryo comprising the genetically modified ES cells is incubated until the blastocyst stage and then implanted into a surrogate mother to produce an F0 mouse. Mice bearing the genetically modified genomic locus can be identified via modification of allele (MOA) assay as described herein. The resulting F0 generation mouse derived from the genetically modified ES cells is crossed to a wild-type mouse to obtain F1 generation offspring. Following genotyping with specific primers and/or probes, F1 pups that are heterozygous for the genetically modified genomic locus are crossed to each other to produce mice that are homozygous for the genetically modified genomic locus.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates, which may need to be independently confirmed.

The described invention may be embodied in other specific forms without departing from the spirit or essential attributes thereof and, accordingly, reference should be made to the appended claims, rather than to the foregoing specification, as indicating the scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Enhanced LTVEC Targeting by a Zinc Finger Nuclease (ZFN)

In order to test if inducing a double-strand break in a gene by a zinc finger nuclease (ZFN) could enhance the targeting of the same gene by an LTVEC (a large BAC-based targeting vector), three electroporations were performed into F1H4 ES cells with an LTVEC targeting the Il2rg gene and plasmids encoding each half of a ZFN pair in the following combinations: (1) 1.5 µg of Il2rg LTVEC alone; (2) 20 µg of Il2rg ZFN-1+20 µg of Il2rg LTVEC ZFN-2+1.5 µg of Il2rg LTVEC; and (3) 20 µg of Il2rg ZFN-1+20 µg of Il2rg ZFN-2 without LTVEC.

ZFN-1 and ZFN-2 used herein were designed to contain (1) zinc finger DNA binding domains that recognize two contiguous target DNA sequences in each strand of the target sequence separated by a 6 bp cleavage site; and (2) FokI nucleases that dimerize and make a double-strand break at the target site. More specifically, the zinc finger domain of ZFN-1 was designed to recognize 5'-AGCTCCAAGGTC-CTC-3' (SEQ ID NO: 1) in the sense strand of exon 1; and the zinc finger domain of ZFN-2 was designed to recognize 5'-GTCTTCATTCGCACT-3' (SEQ ID NO: 2) in the antisense strand of exon 1 in the Il2rg gene.

The LTVEC (VelociGene MAID 5057L1) was designed to delete the approximately 3,000 base pair (3 kb) of the Il2rg gene, including all of the coding sequence for the IL-2 receptor gamma chain and to replace the endogenous sequence with a selection cassette that expresses hygromycin phosphotransferase, which imparts resistance to hygromycin B. LTVEC 5057L1 is derived from parental BAC clone 290o15 isolated from a commercially available BAC library (BAC ES Release 2; Incyte Genomics) and contains two large homology arms with about 90 kb (homology arm 1) and about 8 kb (homology arm 2).

For electroporations (1) and (2), hygromycin B-resistant colonies were isolated. For electroporation (3), colonies were allowed to form without drug selection. Colonies were picked from each electroporation and cultured in 96-well plates, followed by screening for targeting events by loss-of-allele (LOA) assays designed to detect the 3 kb deletion created by correct targeting of the Il2rg gene by the LTVEC. LOA assays were also used to detect cleavage events induced by the ZFN in exon 1.

TABLE 1

LOA assays for the targeted 3 kb deletion

5057U2 assay (intron 2)

| | | |
|---|---|---|
| Forward Primer | 5'-GGAGGGTAGCACGGGAAGAAG-3' | SEQ ID NO: 3 |
| Reverse Primer | 5'-GCTGGCTACCCACTTGATTGG-3' | SEQ ID NO: 4 |
| TaqMan® probe | 5'-TCAAGCAGTCTCTCCCAGCTAACCTCCCT-3' | SEQ ID NO: 5 |

5057D2 assay (intron 7)

| | | |
|---|---|---|
| Forward Primer | 5'-CAGGATGTGGCTGACCAAATG-3' | SEQ ID NO: 6 |
| Reverse Primer | 5'-GGCTCCTAATGCCCTGTAGTTTC-3' | SEQ ID NO: 7 |
| TaqMan® probe | 5'-CCGTCTCTCTGCCTAGCCCACCCT-3' | SEQ ID NO: 8 |

TABLE 2

LOA assay for the ZFN cleavage

| | | |
|---|---|---|
| Forward Primer | 5'-CAGCTGCTCCTGCTGAGG-3' | SEQ ID NO: 9 |
| Reverse Primer | 5'-CCTACCAGCTTTGATGTCTTCATTC-3' | SEQ ID NO: 10 |
| TaqMan® probe | 5'-AGCTCCAAGGTCCTCATGTCCAGT-3' | SEQ ID NO: 11 |

TABLE 3

Comparison of Targeting Efficiency of LTVECs

| EP | LTVEC (µg) | ZFN-1 (µg) | ZFN-2 (µg) | Number of clones assayed | Clones correctly targeted by LTVEC | Targeting Efficiency (%) | Clones with ZFN Cleavage | ZFN cleavage efficiency (%) |
|---|---|---|---|---|---|---|---|---|
| 1 | 1.5 | 0 | 0 | 26 | 5 | 19.2 | ND[1] | ND[1] |
| 2 | 1.5 | 20 | 20 | 102 | 76 | 74.5 | 7[2] | 6.9 |
| 3 | 0 | 20 | 20 | 192 | 0 | 0 | 6 | 3.1 |

[1] not determined
[2] among the clones that were not correctly targeted by the LTVEC As shown in Table 3, when plasmids encoding a ZFN designed to cleave a site in a target gene were combined with an LTVEC that targets the same gene (EP #2), a significant enhancement (approximately about 4-fold increase in the experiment described) of targeting efficiency was achieved compared to the LTVEC alone (EP #1).

While the described invention has been described with reference to the specific embodiments thereof, it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for modifying a target genomic locus in a mouse embryonic stem (ES) cell, comprising:
   (a) introducing into the mouse ES cell:
      (i) a zinc finger nuclease (ZFN) that makes a double-strand break at or near a target genomic locus; and
      (ii) a large targeting vector (LTVEC) comprising an insert nucleic acid flanked by an upstream homology arm and a downstream homology arm,
      wherein the insert nucleic acid ranges from 5 kb to 30 kb in length,
      wherein the sum total of the upstream and downstream homology arms is at least 10 kb in length,
      wherein each of the upstream and downstream homology arms is between 5 kb and 200 kb in length, and
      wherein the LTVEC ranges from 50 kb to 300 kb in length;
   (b) assaying the mouse ES cell for integration of the insert nucleic acid into the target genomic locus, wherein the integration results in deletion of an endogenous nucleic acid sequence at the target genomic locus and replacement with the insert nucleic acid; and
   (c) selecting a targeted mouse ES cell comprising the insert nucleic acid in the target genomic locus, wherein combined use of the LTVEC with the ZFN results in an increased targeting efficiency compared to use of the LTVEC alone.

2. The method of claim 1, wherein the targeting efficiency is increased at least two-fold compared to use of the LTVEC alone.

3. The method of claim 1, wherein:
   (I) the ZFN is an expression construct comprising a nucleic acid sequence encoding a ZFN protein, and wherein the nucleic acid is operably linked to a promoter active in the cell; or
   (II) the ZFN is an mRNA encoding a ZFN protein.

4. The method of claim 1, wherein a target sequence of the ZFN is located in an intron, an exon, a promoter, a promoter regulatory region, or an enhancer region in the target genomic locus.

5. The method of claim 1, wherein the LTVEC is from 50 kb to 100 kb.

6. The method of claim 1, wherein the LTVEC is from 100 kb to 200 kb.

7. The method of claim 1, wherein the LTVEC is from 200 kb to 300 kb.

8. The method of claim 1, wherein the total sum of the upstream and the downstream homology arms is from 10 kb to 200 kb.

9. The method of claim 8, wherein the total sum of the upstream and the downstream homology arms is from 10 kb to 100 kb.

10. The method of claim 1, wherein:
(I) the insert nucleic acid comprises a selection cassette;
(II) the insert nucleic acid comprises a reporter gene;
(III) the insert nucleic acid comprises a human nucleic acid sequence;
(IV) the insert nucleic acid comprises a nucleic acid flanked by site-specific recombination target sequences; or
(V) the insert nucleic acid comprises a conditional allele.

11. The method of claim 1, wherein:
(I) the insert nucleic acid comprises a nucleic acid sequence homologous to the replaced nucleic acid sequence at the target genomic locus of the mouse ES cell;
(II) the insert nucleic acid comprises a nucleic acid sequence orthologous to the replaced nucleic acid sequence at the target genomic locus of the mouse ES cell; or
(III) the insert nucleic acid comprises a nucleic acid sequence from a species that is different from the mouse.

12. The method of claim 1, wherein the insert nucleic comprises a genomic nucleic acid sequence that encodes a human immunoglobulin heavy chain variable region amino acid sequence.

13. The method of claim 1, wherein the insert nucleic comprises a genomic nucleic acid sequence that encodes a human immunoglobulin light chain variable region amino acid sequence.

14. The method of claim 13, wherein the genomic nucleic acid sequence comprises an unrearranged human κ and/or λ light chain variable region nucleic acid sequence.

15. The method of claim 13, wherein the genomic nucleic acid sequence comprises a rearranged human κ and/or λ light chain variable region nucleic acid sequence.

16. The method of claim 1, wherein the insert nucleic acid comprises a human disease allele.

17. The method of claim 12, wherein the insert nucleic acid comprises a rearranged human immunoglobulin heavy chain variable region nucleic acid sequence operably linked to an immunoglobulin heavy chain constant region nucleic acid sequence.

18. The method of claim 12, wherein the insert nucleic acid comprises an unrearranged human immunoglobulin heavy chain variable region nucleic acid sequence operably linked to an immunoglobulin heavy chain constant region nucleic acid sequence.

19. The method of claim 17, wherein the immunoglobulin heavy chain constant region sequence is a mouse immunoglobulin heavy chain constant region sequence, a human immunoglobulin heavy chain constant region sequence, or a combination thereof.

20. The method of claim 17, wherein the immunoglobulin heavy chain constant region nucleic acid sequence is selected from a $C_H1$, a hinge, a $C_H2$, a $C_H3$, and a combination thereof.

21. The method of claim 18, wherein the immunoglobulin heavy chain constant region sequence is a mouse immunoglobulin heavy chain constant region sequence, a human immunoglobulin heavy chain constant region sequence, or a combination thereof.

22. The method of claim 18, wherein the immunoglobulin heavy chain constant region nucleic acid sequence is selected from a $C_H1$, a hinge, a $C_H2$, a $C_H3$, and a combination thereof.

23. The method of claim 14, wherein the insert nucleic acid comprises an unrearranged human κ or λ light chain variable region nucleic acid sequence operably linked to a mouse or human immunoglobulin light chain constant region nucleic acid sequence selected from a κ light chain constant region nucleic acid sequence and a λ light chain constant region nucleic acid sequence.

24. The method of claim 15, wherein the insert nucleic acid comprises a rearranged human κ or λ light chain variable region nucleic acid sequence operably linked to a mouse or human immunoglobulin light chain constant region nucleic acid sequence selected from a κ light chain constant region nucleic acid sequence and a λ light chain constant region nucleic acid sequence.

25. The method of claim 1, wherein selecting step (b) is carried out via a modification of allele (MOA) assay.

26. The method of claim 1, wherein integration of the insert nucleic acid into the target genomic locus results in a knockout, a knock-in, a point mutation, a domain swap, an exon swap, an intron swap, a regulatory sequence swap, a gene swap, or a combination thereof.

27. The method of claim 1, wherein integration of the insert nucleic acid into the target genomic locus results in a deletion of an endogenous gene at the target genomic locus.

28. The method of claim 1, further comprising:
(c) introducing the modified mouse ES cell into a pre-morula stage embryo;
(d) incubating the embryo until the blastocyst stage and implanting the embryo into a surrogate mother to produce an F0 mouse; and
(e) identifying a mouse bearing the genetically modified genomic locus.

* * * * *

SEQUENCE LISTING

<160> NUMBER OF SEQ ID NOS: 11

<210> SEQ ID NO 1
<211> LENGTH: 15
<212> TYPE: DNA
<213> ORGANISM: Artificial
<220> FEATURE:
<223> OTHER INFORMATION: Synthetic

<400> SEQUENCE: 1
agctccaagg tcctc                15

<210> SEQ ID NO 2
<211> LENGTH: 15
<212> TYPE: DNA
<213> ORGANISM: Artificial
<220> FEATURE:
<223> OTHER INFORMATION: Synthetic

<400> SEQUENCE: 2
gtcttcattc gcact                15

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
ggagggtagc acgggaagaa g                21

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
gctggctacc cacttgattg g                21

<210> SEQ ID NO 5
<211> LENGTH: 29
<212> TYPE: DNA
<213> ORGANISM: Artificial
<220> FEATURE:
<223> OTHER INFORMATION: Synthetic

<400> SEQUENCE: 5
tcaagcagtc tctcccagct aacctccct                29

<210> SEQ ID NO 6
<211> LENGTH: 21
<212> TYPE: DNA
<213> ORGANISM: Artificial
<220> FEATURE:
<223> OTHER INFORMATION: Synthetic

<400> SEQUENCE: 6
caggatgtgg ctgaccaaat g                21

<210> SEQ ID NO 7
<211> LENGTH: 23
<212> TYPE: DNA
<213> ORGANISM: Artificial

```
<220> FEATURE:
<223> OTHER INFORMATION: Synthetic

<400> SEQUENCE: 7
ggctcctaat gccctgtagt ttc                                                 23

<210> SEQ ID NO 8
<211> LENGTH: 24
<212> TYPE: DNA
<213> ORGANISM: Artificial
<220> FEATURE:
<223> OTHER INFORMATION: Synthetic

<400> SEQUENCE: 8
ccgtctctct gcctagccca ccct                                                24

<210> SEQ ID NO 9
<211> LENGTH: 18
<212> TYPE: DNA
<213> ORGANISM: Artificial
<220> FEATURE:
<223> OTHER INFORMATION: Synthetic

<400> SEQUENCE: 9
cagctgctcc tgctgagg                                                       18

<210> SEQ ID NO 10
<211> LENGTH: 25
<212> TYPE: DNA
<213> ORGANISM: Artificial
<220> FEATURE:
<223> OTHER INFORMATION: Synthetic

<400> SEQUENCE: 10
cctaccagct ttgatgtctt cattc                                               25

<210> SEQ ID NO 11
<211> LENGTH: 24
<212> TYPE: DNA
<213> ORGANISM: Artificial
<220> FEATURE:
<223> OTHER INFORMATION: Synthetic

<400> SEQUENCE: 11
agctccaagg tcctcatgtc cagt                                                24
```